United States Patent
Swanson et al.

(10) Patent No.: US 10,751,122 B2
(45) Date of Patent: Aug. 25, 2020

(54) PROTECTIVE SYSTEMS AND METHODS FOR USE DURING ABLATION PROCEDURES

(75) Inventors: David K. Swanson, Campbell, CA (US); Ara Stephanian, Davis, CA (US)

(73) Assignee: AtriCure, Inc., Mason, OH (US)

( * ) Notice: Subject to any disclaimer, the term of this patent is extended or adjusted under 35 U.S.C. 154(b) by 579 days.

(21) Appl. No.: 13/074,960

(22) Filed: Mar. 29, 2011

(65) Prior Publication Data
US 2011/0238059 A1 Sep. 29, 2011

Related U.S. Application Data

(60) Provisional application No. 61/318,474, filed on Mar. 29, 2010.

(51) Int. Cl.
*A61B 18/16* (2006.01)
*A61B 18/12* (2006.01)

(52) U.S. Cl.
CPC .......... *A61B 18/16* (2013.01); *A61B 18/1233* (2013.01); *A61B 2018/1253* (2013.01); *A61B 2018/165* (2013.01)

(58) Field of Classification Search
CPC ...... A61B 2017/002; A61B 2017/0212; A61B 2017/0292; A61B 19/08; A61B 18/12; A61B 18/1206; A61B 18/1233; A61B 18/00; A61B 2018/00351; A61B 2018/00357; A61B 2018/00369; A61B 2018/12; A61B 2018/1206; A61B 2018/1293; A61B 19/40; A61F 7/08; A61F 7/10

USPC ...................................................... 606/33, 34
See application file for complete search history.

(56) References Cited

U.S. PATENT DOCUMENTS

| | | | |
|---|---|---|---|
| 4,754,757 A | 7/1988 | Feucht | |
| 4,947,843 A * | 8/1990 | Wright | A61F 7/10 128/846 |
| 6,296,636 B1 | 10/2001 | Cheng et al. | |
| 6,830,569 B2 | 12/2004 | Thompson et al. | |
| 6,939,350 B2 | 9/2005 | Phan | |
| 6,997,735 B2 | 2/2006 | Ehr et al. | |
| 7,247,155 B2 | 7/2007 | Hoey et al. | |
| 7,285,119 B2 | 10/2007 | Stewart et al. | |
| 7,288,090 B2 | 10/2007 | Swanson | |
| 7,566,332 B2 | 7/2009 | Jarrard et al. | |
| 2001/0021848 A1 | 9/2001 | Fleenor et al. | |
| 2002/0010466 A1 * | 1/2002 | Alleyne | 606/61 |
| 2002/0198523 A1 | 12/2002 | Behl | |
| 2003/0045871 A1 | 3/2003 | Jain et al. | |
| 2003/0078644 A1 | 4/2003 | Phan | |

(Continued)

OTHER PUBLICATIONS

Non-Final Office Action dated Apr. 24, 2014 for U.S. Appl. No. 13/074,867 (12 pages).

*Primary Examiner* — Eun Hwa Kim
(74) *Attorney, Agent, or Firm* — Levine Bagade Han LLP

(57) ABSTRACT

Systems and methods provide protection for patient tissue during radiofrequency ablation treatments. Exemplary techniques involve placing a conductive or semiconductive pad assembly near a target tissue, and administering electrical current through the target tissue while protecting adjacent tissue with the pad assembly. The pad assembly may include a material having an electrical conductivity value that is equal to or greater than the electrical conductivity value of the target tissue.

19 Claims, 18 Drawing Sheets

(56) References Cited

U.S. PATENT DOCUMENTS

| | | |
|---|---|---|
| 2003/0144653 A1 | 7/2003 | Francischelli et al. |
| 2003/0199867 A1 | 10/2003 | Wellman |
| 2004/0025377 A1* | 2/2004 | Brannon .................. 36/59 R |
| 2004/0097916 A1 | 5/2004 | Thompson et al. |
| 2004/0220560 A1 | 11/2004 | Briscoe |
| 2005/0101947 A1 | 5/2005 | Jarrard et al. |
| 2005/0107731 A1* | 5/2005 | Sessions ..................... 602/41 |
| 2006/0041251 A1 | 2/2006 | Odell et al. |
| 2006/0041253 A1 | 2/2006 | Newton et al. |
| 2006/0089637 A1 | 4/2006 | Werneth et al. |
| 2006/0111700 A1* | 5/2006 | Kunis ............. A61B 18/1492 606/41 |
| 2007/0049914 A1 | 3/2007 | Eggleston |
| 2007/0049919 A1 | 3/2007 | Lee et al. |
| 2007/0049925 A1 | 3/2007 | Phan et al. |
| 2007/0167942 A1 | 7/2007 | Rick |
| 2007/0244478 A1 | 10/2007 | Bahney |
| 2008/0015563 A1 | 1/2008 | Hoey et al. |
| 2008/0071263 A1 | 3/2008 | Blaha |
| 2008/0077126 A1* | 3/2008 | Rashidi ..................... 606/34 |
| 2008/0281312 A1 | 11/2008 | Werneth et al. |
| 2009/0036885 A1 | 2/2009 | Gregg |
| 2009/0326511 A1* | 12/2009 | Shivkumar ................ 604/506 |
| 2011/0238058 A1 | 9/2011 | van den Biggelaar et al. |

* cited by examiner

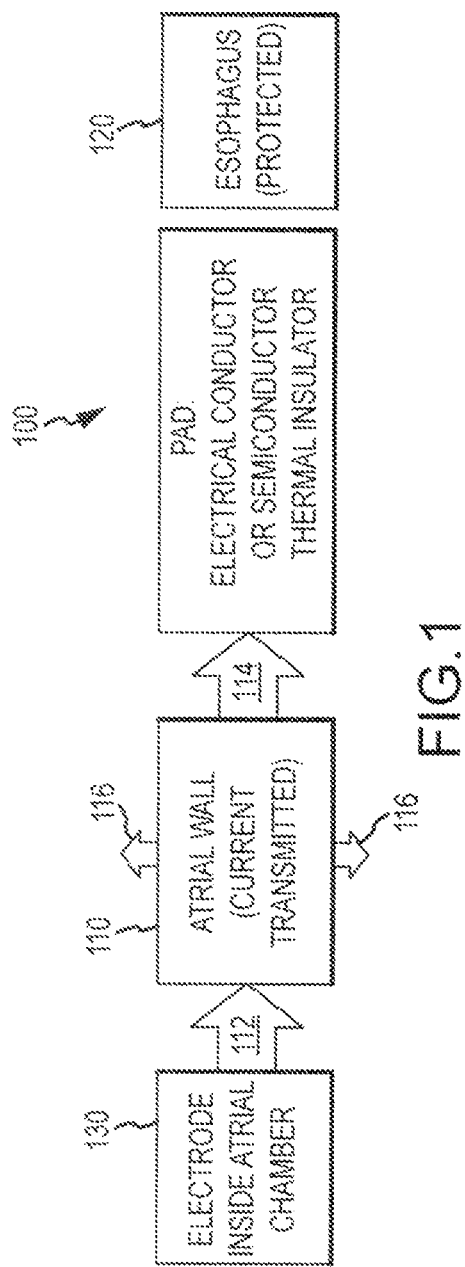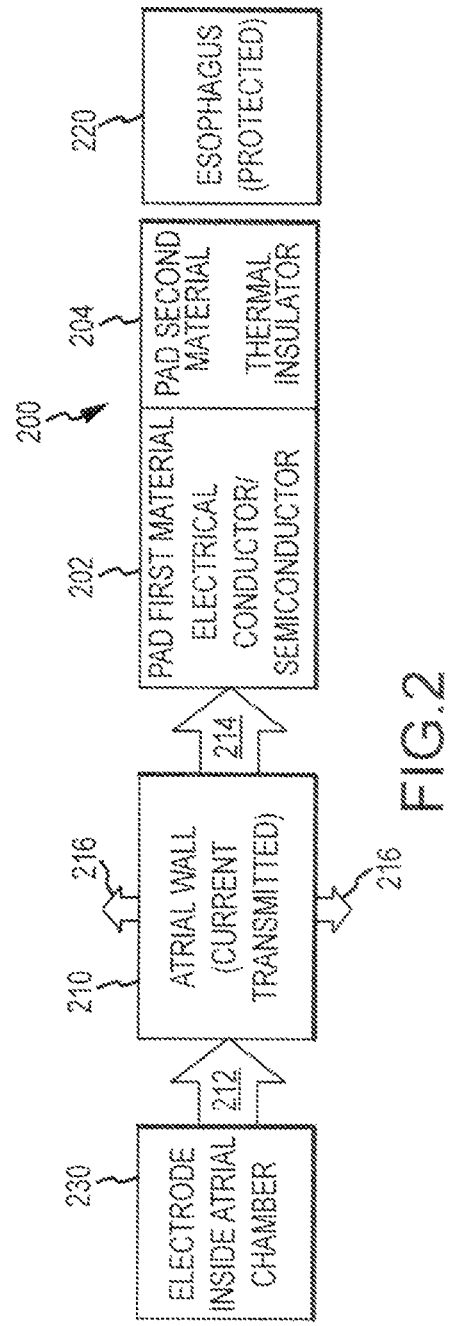

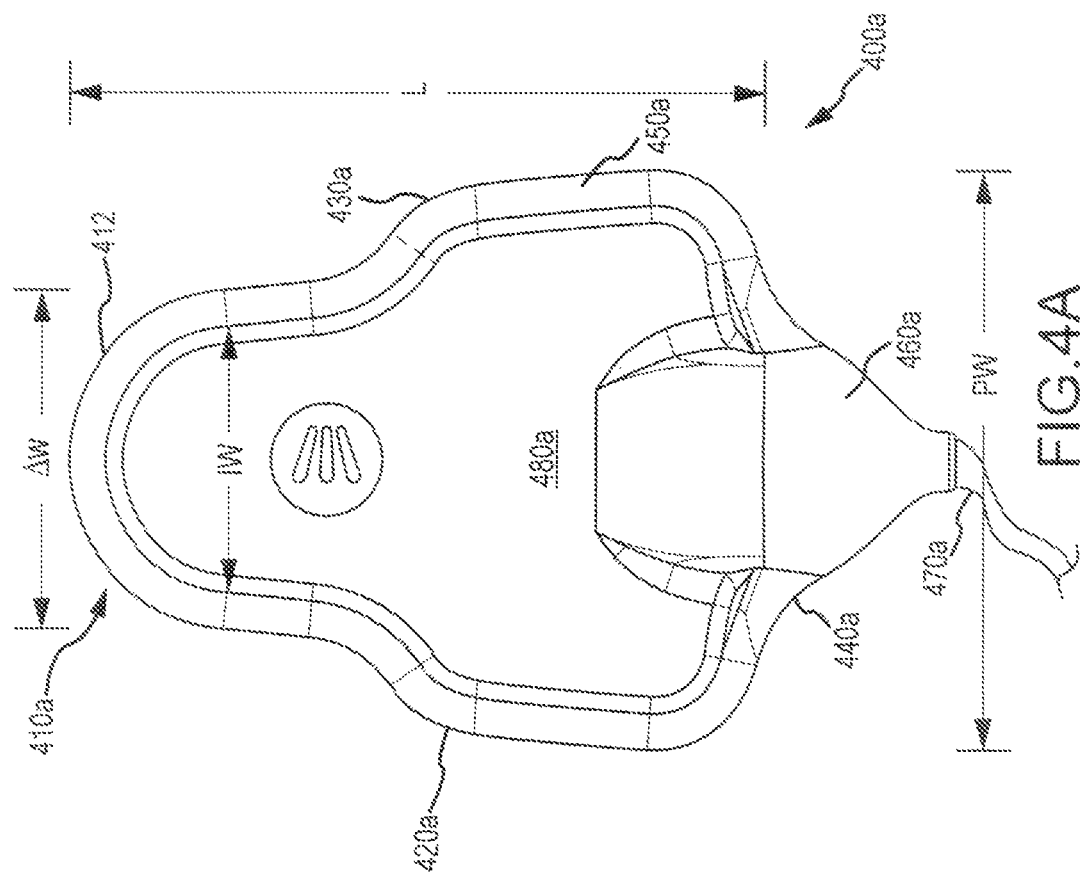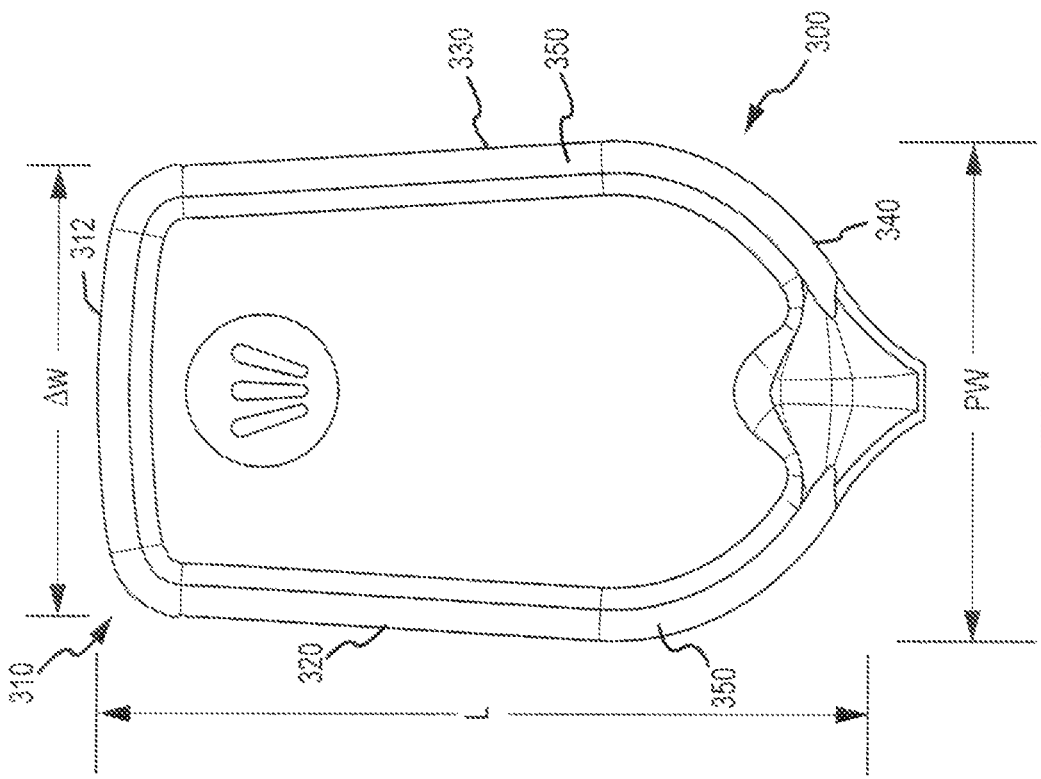

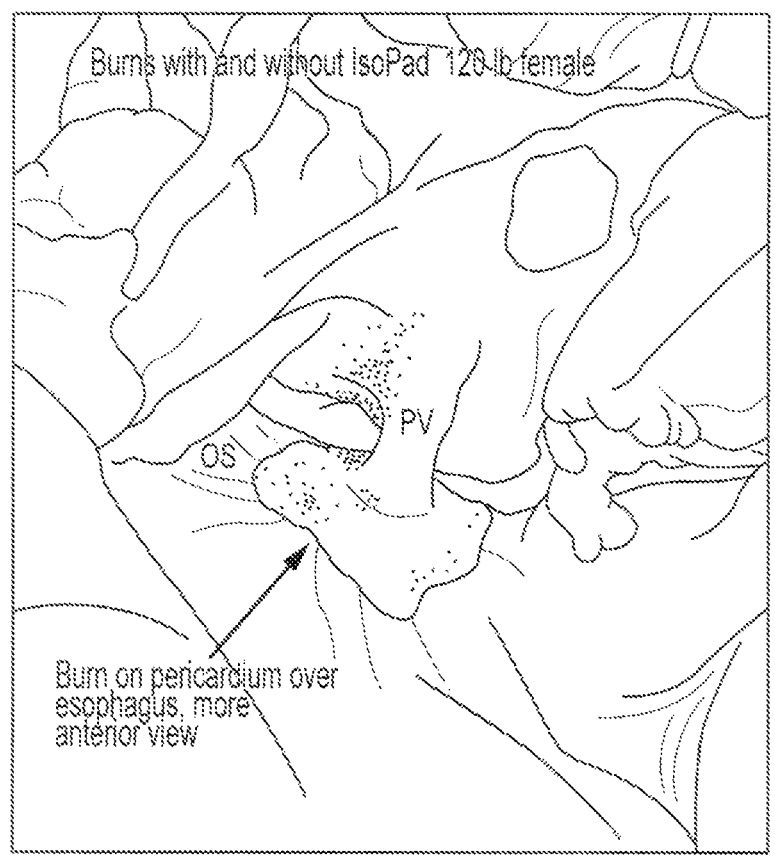
FIG.7B1

PROTECTIVE SYSTEMS AND METHODS FOR USE DURING ABLATION PROCEDURES

CROSS-REFERENCES TO RELATED APPLICATIONS

This application is a nonprovisional of, and claims the benefit of priority to, U.S. Provisional Patent Application No. 61/318,474 filed Mar. 29, 2010. This application is also related to U.S. patent application Ser. No. 13/074,867 filed Mar. 29, 2011 and U.S. Pat. No. 7,288,090. The content of each of the above filings is incorporated herein by reference for all purposes.

BACKGROUND OF THE INVENTION

Embodiments of the present invention related generally to the field of medical devices and methods, and in particular to therapeutic modalities involving tissue ablation or lesion formation.

There are many instances where it is beneficial to perform a therapeutic intervention in a patient, using a system that is inserted within the patient's body. One exemplary therapeutic intervention involves the formation of therapeutic lesions in the patient's heart tissue to treat cardiac conditions such as atrial fibrillation, atrial flutter, and arrhythmia. Therapeutic lesions may also be used to treat conditions in other regions of the body including, but not limited to, the prostate, liver, brain, gall pod, uterus, and other solid organs. Typically, the lesions are formed by ablating tissue with one or more electrodes. Electromagnetic radio frequency ("RF") energy applied by the electrode heats and eventually kills or ablates the tissue to form a lesion. During the ablation of soft tissue (e.g. tissue other than blood, bone and connective tissue), tissue coagulation occurs, which leads to tissue death. Thus, references to the ablation of soft tissue are typically references to soft tissue coagulation. "Tissue coagulation" can refer to the process of cross linking proteins in tissue to cause the tissue to jell. In soft tissue, it is the fluid within the tissue cell membranes that jells to kill the cells, thereby killing the tissue. Depending on the procedure, a variety of different electrophysiology devices may be used to position one or more electrodes at the target location. Electrodes can be connected to power supply lines and, in some instances, the power to the electrodes can be controlled on an electrode-by-electrode basis. Examples of electrophysiology devices include catheters, surgical probes, and clamps.

Currently known surgical probes which can be used to create lesions often include a handle, a relatively short shaft that is from 4 inches to 18 inches in length and either rigid or relatively stiff, and a distal section that is from 1 inch to 10 inches in length and either malleable or somewhat flexible. One or more electrodes are carried by the distal section. Surgical probes are used in epicardial and endocardial procedures, including open heart procedures and minimally invasive procedures where access to the heart is obtained via a thoracotomy, thoracostomy or median sternotomy. Exemplary surgical probes are disclosed in U.S. Pat. No. 6,142,994, the content of which is incorporated herein by reference.

Clamps, which have a pair of opposable clamp members that may be used to hold a bodily structure or a portion thereof, are used in many types surgical procedures. Lesion creating electrodes have also been secured to certain types of clamps. Examples of clamps which carry lesion creating electrodes are discussed in U.S. Pat. No. 6,142,994, and U.S. Patent Publication Nos. 2003/0158549, 2004/0059325, and 2004/024175, the contents of which are incorporated herein by reference. Such clamps can be useful when the physician intends to position electrodes on opposite sides of a body structure in a bipolar arrangement.

Atrial fibrillation (AF) can refer to a heart beat rhythm disorder (or "cardiac arrhythmia") in which the upper chambers of the heart known as the atria quiver rapidly instead of beating in a steady rhythm. This rapid quivering reduces the heart's ability to properly function as a pump. AF is a common clinical condition, and presents a substantial medical issue to aging populations. AF is costly to health systems, and can cause complications such as thrombo-embolism, heart failure, electrical and structural remodeling of the heart, and even death. Relatedly, AF typically increases the risk of acquiring a number of potentially deadly complications, including thrombo-embolic stroke, dilated cardiomyopathy, and congestive heart failure. Quality of life is also impaired by common AF symptoms such as palpitations, chest pain, dyspnea, fatigue and dizziness. People with AF have, on average, a five-fold increase in morbidity and a two-fold increase in mortality compared to people with normal sinus rhythm. One of every six strokes in the U.S. (some 120,000 per year) occurs in patients with AF, and the condition is responsible for one-third of all hospitalizations related to cardiac rhythm disturbances (over 360,000 per year), resulting in billions of dollars in annual healthcare expenditures. The likelihood of developing AF increases dramatically as people age; the disorder is found in about 1% of the adult population as a whole, and in about 6% of those over age 60. By age 80, about 9% of people (one in 11) will have AF. According to a recent statistical analysis, the prevalence of AF in the U.S. will more than double by the year 2050, as the proportion of elderly increases. A recent study called The Anticoagulation and Risk Factors in Atrial Fibrillation (ATRIA) study, published in the Spring of 2001 in the Journal of the American Medical Association (JAMA), found that 2.3 million U.S. adults currently have AF and this number is likely to increase over the next 50 years to more than 5.6 million, more than half of whom will be age 80 or over.

As the prevalence of AF increases, so will the number of people who develop debilitating or life-threatening complications, such as stroke. According to Framingham Heart Study data, the stroke rate in AF patients increases from about 3%/year of those aged 50-59 to more than 7%/year of those aged 80 and over. AF is responsible for up to 35% of the strokes that occur in people older than age 85. Efforts to prevent stroke in AF patients have so far focused primarily on the use of anticoagulant and antiplatelet drugs, such as warfarin and aspirin. Long-term warfarin therapy is recommended for all AF patients with one or more stroke risk factors, including all patients over age 75. Studies have shown, however, that warfarin tends to be under prescribed for AF. Despite the fact that warfarin reduces stroke risk by 60% or more, only 40% of patients age 65-74 and 20% of patients over age 80 take the medication, and probably fewer than half are on the correct dosage. Patient compliance with pharmacological intervention such as warfarin is problematic, and the drug requires vigilant blood monitoring to reduce the risk of bleeding complications.

More recently, the focus has shifted toward surgical or catheter ablation options to treat or effect a cure for AF. The ablation techniques for producing lines of electrical isolation are now replacing the so-called Maze procedure. The Maze procedure uses a set of transmural surgical incisions on the atria to create fibrous scars in a prescribed pattern. This procedure was found to be highly efficacious but was associated with a high morbidly rate. The more recent approach of making lines of scar tissue with modern ablation technology has enabled the electrophysiologist or cardiac surgeon to create the lines of scar tissue more safely. Ideally, re entrant circuits that perpetuate AF can be interrupted by the connected lines of scar tissue, and the goal of achieving normal sinus rhythm in the heart may be achieved.

Electrophysiologists often classify AF by the "three Ps": paroxysmal, persistent, or permanent. Paroxysmal AF, typically characterized by sporadic, usually self-limiting episodes lasting less than 48 hours, is usually the most amenable to treatment, while persistent or permanent AF can be much more resistant to known therapies. Researchers now know that AF is a self-perpetuating disease and that abnormal atrial rhythms tend to initiate or trigger more abnormal rhythms. Thus, the more episodes a patient experiences and the longer the episodes last, the less chance of converting the heart to a persistent normal rhythm, regardless of the treatment method.

AF is often characterized by circular waves of electrical impulses that travel across the atria in a continuous cycle, causing the upper chambers of the heart to quiver rapidly. At least six different locations in the atria have been identified where these waves can circulate, a finding that paved the way for maze-type ablation therapies. More recently, researchers have identified the pulmonary veins as perhaps the most common area where AF-triggering foci reside. Triggers for intermittent AF and drivers for permanent AF can be located at various places on the heart, such as the atria. For example, where triggers or drivers are located near the pulmonary veins, it follows that treatment may involve electrical isolation of the pulmonary veins. Technologies designed to isolate the pulmonary veins or ablate specific pulmonary foci appear to be very promising and are the focus of much of the current research in catheter-based ablation techniques.

Certain cardiac surgical procedures involve administering ablative energy to the cardiac tissue in an attempt to create a transmural lesion on the tissue. However, with some current ablation approaches, including various temperature-based RF technologies, there may be difficulties in making transmural lesions as desired. Thus, although cardiac ablation devices and methods are currently available and provide real benefits to patients in need thereof, many advances may still be made to provide improved devices and methods for ablating epicardial tissue to treat AF and other arrhythmias. For example, there continues to be a need for improved systems and methods that can effectively deliver ablative energy to patient target tissue in a way that does not damage adjacent tissue. Embodiments of the present invention provide solutions that address the problems described above, and hence provide answers to at least some of these outstanding needs.

BRIEF SUMMARY OF THE INVENTION

Embodiments of the present invention provide systems and method for delivering ablative radiofrequency electric current through target tissue in a patient, while inhibiting damage to other patient tissue located near to the target tissue. For example, techniques may involve transmitting ablative energy through the posterior wall of the patient's left atrium without damaging or perforating the patient's esophagus. Hence, such approaches can help to reduce the incidence of atrioesophageal fistula (which is often fatal) or other complications associated with catheter AF ablation, such as left or right phrenic nerve injury, which can paralyze the left or right half of the diaphragm respectively. Relatedly, aspects of the instant invention enable physicians and other medical operators to safely and effectively achieve electrical isolation of one or more of the pulmonary veins (PVs) or selected areas of the posterior left atrium, even in patients where the esophagus is positioned in close proximity with the PVs or left atrium.

In one aspect, embodiments of the present invention encompass systems and methods for delivering an ablative radiofrequency electric current through a posterior wall of a patient's left atrium. In some cases, methods include placing a radiofrequency electrode within the left atrial chamber of the patient's heart, placing a pad assembly between the patient's esophagus and the posterior wall of the left atrium, placing a return pad on the patient' skin, and transmitting the ablative radiofrequency electric current from the electrode, through the atrial wall, into the pad assembly, and to the return pad. Optionally, the pad assembly may include a material having a volume resistivity within a range from about 2 ohm-cm to about 2000 ohm-cm as measured at 1 MHz. In some cases, the posterior wall of the left atrium has an electrical conductivity value, and the pad assembly includes a material having an electrical conductivity value that is equal to or greater than the electrical conductivity value of the posterior wall of the left atrium. In some cases, the electrical conductivity value of the material is within a range from about 20 (ohm-cm) to about 500 (ohm-cm). In some cases, the material has a thermal conductivity value that is within a range from about 0.05 W/m° C. to about 1.0 W/m° C. In exemplary embodiments, the pad assembly can include an anterior portion material having an electrical conductivity value within a range from about 20 (ohm-cm) to about 500 (ohm-cm) coupled with a posterior portion material having a thermal conductivity value that is within a range from about W/m° C. to about 1.0 W/m° C. Optionally, the step of placing the pad assembly between the patient's atrial wall and esophagus can include positioning the pad assembly between epicardial tissue and pericardial tissue of patient's heart. In some cases, methods may include withdrawing the pad assembly from the patient by pulling on a tether of the pad assembly. In some cases, the pad assembly includes an anterior portion and a posterior portion, and the step of placing the pad assembly between the patient's atrial wall and esophagus includes positioning the pad assembly so that the anterior portion faces toward the atrial wall and the posterior portion faces toward the esophagus. In some cases, the step of transmitting the ablative radiofrequency electric current from the electrode through the atrial wall and into the pad assembly includes transmitting the current through endocardial tissue of the patient's left atrium. In some cases, the step of transmitting the ablative radiofrequency electric current from the electrode through the atrial wall and into the pad assembly includes transmitting the current through epicardial tissue of the patient's left atrium.

In another aspect, embodiments of the present invention include systems for administering ablative radiofrequency electric current therapy to a patient. Exemplary systems can include an electrosurgical unit assembly having an electrode configured for placement within the patient's left atrial chamber. The electrode can be configured to transmit an ablative radiofrequency electric current. Systems may also include a pad assembly configured for placement between the patient's esophagus and the posterior wall of the patient's left atrium. The pad assembly can be configured to receive the ablative radiofrequency electric current transmitted by the electrode. Further, systems may include a return pad configured for placement on the patient's skin. The return pad can be in operative association with the electrosurgical unit assembly and configured to receive the ablative radiofrequency electric current delivered from the pad assembly. In some cases, the posterior wall of the left atrium has an electrical conductivity value, and the pad assembly includes a material having an electrical conductivity value that is equal to or greater than the electrical conductivity value of the posterior wall of the left atrium. In some cases, the electrical conductivity value of the material is within a range from about 20 (ohm-cm) to about 500 (ohm-cm). In some cases, the material has a thermal conductivity value that is within a range from about 0.05 W/m° C. to about 1.0 W/m° C. Optionally, the pad assembly can include an anterior portion material having an electrical conductivity value within a range from about 20 (ohm-cm) to about 500 (ohm-cm) coupled with a posterior portion material having a thermal conductivity value that is within a range from about 0.05 W/m° C. to about 1.0 W/m° C. In some cases, the pad assembly is positionable between epicardial tissue and pericardial tissue of patient's heart. In some cases, the pad assembly includes a tether mechanism. According to exemplary embodiments, the pad assembly can include an anterior portion and a posterior portion, and the pad assembly can be positionable between the patient's atrial wall and esophagus so that the anterior portion faces toward the atrial wall and the posterior portion faces toward the esophagus.

In still another aspect, embodiments of the present invention encompass systems and methods for preventing or inhibiting injury to a patient's esophagus during delivery of an ablative current through a posterior wall of the patient's left atrium. Exemplary methods may include placing an electrode within the left atrial chamber of the patient's heart, placing a pad assembly between the patient's esophagus and the posterior wall of the left atrium, transmitting the radiofrequency ablative electric current from the electrode, through the atrial wall, and into the pad, and preventing or inhibiting injury to the patient's esophagus with the pad assembly. In some methods, the temperature of the patient's pericardial tissue posterior to the left atrium remains below 50° C. during transmission of the radiofrequency ablative electric current through the atrial wall. Some methods may further include anchoring the pad assembly in place during transmission of the radiofrequency ablative electric current using an anchor means of the pad assembly. In some methods, the step of placing the pad assembly between the patient's esophagus and the posterior wall of the left atrium includes placing the pad assembly within the pericardial space of the patient's heart.

In yet another aspect, embodiments of the present invention encompass systems and methods for delivering or administering ablative radiofrequency electric current therapy to a patient. Exemplary systems may include an electrosurgical unit assembly having an electrode configured for placement within the patient's left atrial chamber. The electrode can be configured to transmit an ablative radiofrequency electric current. Systems may also include a pad assembly configured for placement between the patient's esophagus and the posterior wall of the patient's left atrium. The pad assembly can be configured to receive the ablative radiofrequency electric current transmitted by the electrode and to return the current to the electrosurgical unit.

In another aspect, embodiments of the present invention encompass methods for delivering an ablative radiofrequency electric current through a target tissue of a patient, which can include, for example, placing a radiofrequency electrode at or near the target tissue, and placing a pad assembly between the target tissue and a protected tissue of the patient. The protected tissue can be adjacent to the target tissue. Methods may further include placing a return pad on the patient' skin, and transmitting the ablative radiofrequency electric current from the electrode, through the target tissue, into the pad assembly, and to the return pad. In some cases, the target tissue includes a tumor tissue. Relatedly, the tumor tissue can include a prostate tumor tissue, a kidney tumor tissue, a liver tumor tissue, a lung tumor tissue, or the like.

In still a further aspect, embodiments of the present invention encompass systems for administering ablative radiofrequency electric current therapy to a patient, which can include, for example, an electrosurgical unit assembly having an electrode configured for placement at or near a target tissue of the patient. The electrode can be configured to transmit an ablative radiofrequency electric current. Systems may also include a pad assembly configured for placement between the patient's target tissue and a protected tissue of the patient, where the protected tissue is adjacent to the target tissue. The pad assembly can be configured to receive the ablative radiofrequency electric current transmitted by the electrode. Additionally, systems may include a return pad configured for placement on the patient's skin. The return pad can be in operative association with the electrosurgical unit assembly and configured to receive the ablative radiofrequency electric current delivered from the pad assembly.

In yet another aspect, embodiments of the present invention encompass methods for preventing or inhibiting injury to a protected tissue of a patient during delivery of an ablative current through a target tissue of the patient. Exemplary methods may include placing an electrode at or near the target tissue, placing a pad assembly between the patient's target tissue and protected tissue, transmitting the radiofrequency ablative electric current from the electrode, through the target tissue, and into the pad, and preventing or inhibiting injury to the patient's protected tissue with the pad assembly. In some cases, the target tissue includes a tumor tissue. Relatedly, the tumor tissue can include a prostate tumor tissue, a kidney tumor tissue, a liver tumor tissue, a lung tumor tissue, or the like.

In one aspect, embodiments of the present invention encompass systems for administering ablative radiofrequency electric current therapy to a patient. For example, a system may include an electrosurgical unit assembly having an electrode configured for placement at or near a target tissue of the patient. The electrode can be configured to transmit an ablative radiofrequency electric current. Systems may also include a pad assembly configured for placement between the target tissue and a protected tissue of the patient. The pad assembly can be configured to receive the ablative radiofrequency electric current transmitted by the electrode and to return the current to the electrosurgical unit.

The above described and many other features and attendant advantages of embodiments of the present invention will become apparent and further understood by reference to the following detailed description when considered in conjunction with the accompanying drawings.

BRIEF DESCRIPTION OF THE DRAWINGS

FIG. 1 illustrates aspects of treatment systems and methods according to embodiments of the present invention.

FIG. 2 illustrates aspects of treatment systems and methods according to embodiments of the present invention.

FIG. 3 shows aspects of treatment systems and methods according to embodiments of the present invention.

FIGS. 4A and 4B show aspects of treatment systems and methods according to embodiments of the present invention.

FIGS. 7A, 7B, 7B1, and 7C show aspects of treatment systems and methods according to embodiments of the present invention.

DETAILED DESCRIPTION OF THE INVENTION

Figure 4B:
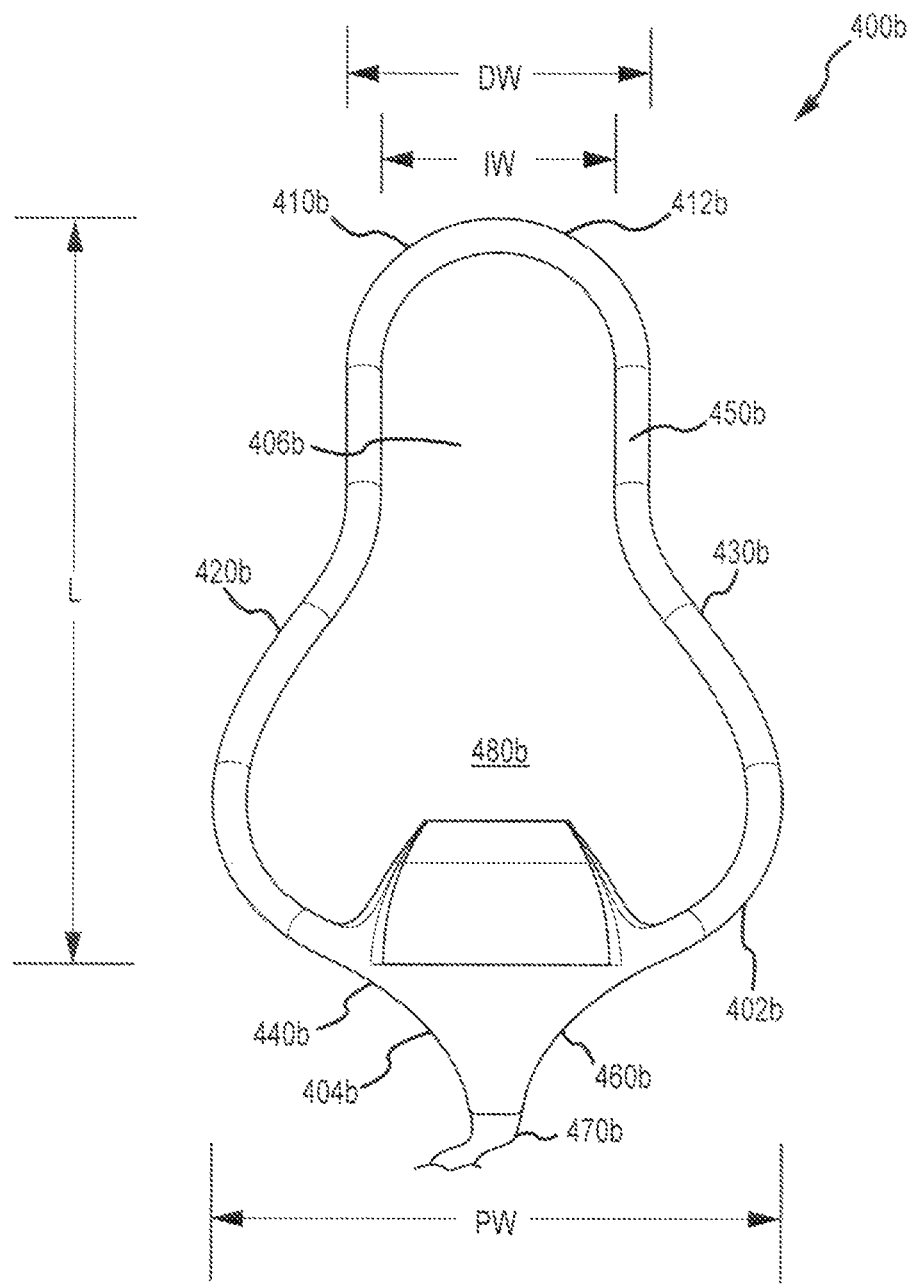

Embodiments of the present invention provide systems and methods for safeguarding patient tissue during radiofrequency ablation treatments. Exemplary techniques involve placing a pad assembly at a sink location on a target tissue, and delivering electrical current at a source location on the tissue, so that the current travels from the source location through the target tissue to the sink location, and into the pad assembly. In this way, the pad assembly can operate to protect other patient tissue which is adjacent to the target tissue from thermal heating and other undesirable side effects of the ablation protocol.

Turning now to the drawings, FIG. 1 schematically shows operational aspects of an exemplary assembly pad 100. As depicted here, assembly pad 100 is placed between the patient's posterior atrial wall 110 and esophagus 120. An electrode 130 is placed inside of the patient's atrium, typically at or near the left posterior atrial wall. Electrical current provided by the electrode passes from an interior portion of the atrial wall (e.g. source location 112), through the atrial wall, to an exterior portion of the atrial wall (e.g. sink location 114). The pad assembly includes a material having an electrical conductivity value that is equal to or greater than the electrical conductivity value of the atrial wall, or target tissue. In some instances, the pad includes a material which is electrically conductive or semiconductive, and thermally insulative. Accordingly, current passes from atrial wall 110 into pad assembly 100. There is minimal lateral current spread or flow 116 away to other locations within atrial wall 110 or to other patient tissue. During the ablation, the delivery of current generates heat build up within atrial wall 110. The material of pad assembly 100 is thermally insulative, so that heat from atrial wall 110 is prevented or inhibited from reaching esophagus 120. Hence, the electrical and thermal conductivity properties of pad assembly 100 act to protect esophagus 120 from unwanted injury or damage.

Accordingly, the pad assembly promotes the propagation or travel path of current posteriorly, instead of laterally, from the atrial wall into the pad body, thus producing a narrow current path through the left atrium. The pad assembly is at least as electrically conductive as the target tissue, so that current goes through the target tissue. This current density operates to heat the atrial tissue. The current passing through the pad assembly provides little heating to the pad because it is electrically conductive. The pad assembly is also thermally insulative, so that thermal transfer does not occur from the heated atrial wall to the esophagus. In some cases, the pad body material has an electrical conductivity value that is greater than that of muscle tissue, and less than that of water.

FIG. 2 illustrates operational aspects of another assembly pad 200, which has been placed into position between the patients' left posterior atrial wall 210 and esophagus 220. An electrode 230 is placed inside of the patient's atrium, at or near left posterior atrial wall 210. Electrical current provided by electrode 230 passes from an interior portion of the atrial wall (e.g. source location 212), through the atrial wall, to an exterior portion of the atrial wall (e.g. sink location 214). The pad assembly includes a first material 202 or anterior portion having an electrical conductivity value that is equal to or greater than the electrical conductivity value of the atrial wall, or target tissue. In some instances, first material 202 is electrically conductive or semiconductive. The pad assembly also includes a second material 204 which is thermally insulative. Accordingly, current passes from atrial wall 210 into pad assembly 200. There is minimal lateral current spread or flow 216 away to other locations within atrial wall 210 or to other patient tissue. During the ablation, the delivery of current generates heat build up within atrial wall 210. The second material 204 or posterior portion of pad assembly 100 is thermally insulative, so that heat from atrial wall 210 is prevented or inhibited from reaching esophagus 220. Hence, the electrical and thermal conductivity properties of pad assembly 200 act to protect esophagus 220 from unwanted injury or damage. In some cases, the second material 204 is not electrically insulative, so that current does not unduly concentrate at the edges and cause local burns there. In exemplary embodiments, the second posterior material 204 has a certain amount of electrical conductivity, and is either more or less electrically conductive than the first anterior material 202. In further exemplary embodiments, it may be desirable to not constrain the first anterior material 202 to be a thermal insulator.

The pad assembly can be configured in any of a variety of shapes appropriate for use in protecting non-cardiac tissues, including the esophagus, from the thermal effects associated with the ablation of the heart. In some instances, the pad assembly may be provided as a flexible thermally insulating pad shaped to fit in the pericardial space and to conform to the posterior portion of the left atrium and right atrium. FIG. 3 shows aspects of a pad assembly 300 according to embodiments of the present invention. Pad assembly 300 includes a distal portion 310 having a flattened or slightly curved leading edge 312. Distal portion 310 also has a width DW, which may be within a range from about 3 cm to about 7 cm. In some cases, width DW is about 5 cm. The lateral sides 320, 330 of pad assembly 300 are tapered. Pad assembly 300 also includes a proximal portion 340 having a width PW, which may be within a range from about 3.5 cm to about 7.5 cm. In some cases, width PW is about 5.5 cm. Further, pad assembly 300 includes a piping or edge 350 that presents a rounded or cylindrical border. In some instances, piping 350 has a diameter with a range from about 0.150 inches to about 0.250 inches. In some instances, piping has a diameter of about 0.200 inches. Pad assembly 300 also has a length L, which may be within a range from about 6 cm to about 10 cm. In some cases, length L is about 8 cm. Overall, pad assembly 300 can be considered to present an oval or ovalized shape configuration.

FIG. 4A shows aspects of a pad assembly 400a according to embodiments of the present invention. Pad assembly 400a includes a distal portion 410a having a rounded leading edge 412a. In some cases, rounded leading edge 412a has a radius of curvature within a range from about 2.1 cm to about 2.5 cm. In some cases, rounded leading edge 412a has a radius of curvature of about 2.3 cm. Distal portion 410a also has a width DW, which may be within a range from about 2.5 cm to about 6.5 cm. In some cases, width DW is about 4.5 cm. Distal portion 410a may also have an inner width IW, between piping portions 450a, within a range from about 2.5 cm to about 4.5 cm. In some cases, width IW is about 3.5 cm. The lateral sides 420a, 430a of pad assembly 400a each present an S-curve shape or profile. Pad assembly 400a also includes a proximal portion 440a having a width PW, which may be within a range from about 5.7 cm to about 9.7 cm. In some cases, width PW is about 7.7 cm. Further, pad assembly 400a includes a piping or edge 450a that presents a rounded or cylindrical border. In some instances, piping 450a has a diameter with a range from about 0.200 inches to about 0.300 inches. In some instances, piping has a diameter of about 0.250 inches. Pad assembly 400a also has a length L, which may be within a range from about 7 cm to about 11 cm. In some cases, length L is about 9 cm. Overall, pad assembly 400a can be considered to present a bell shape configuration. As shown here, pad assembly 400a includes a tether transition portion 460a. Pad assembly 400a may also include a tether assembly 470a attached with a body 480a of the pad assembly via tether transition portion 460a. Tether assembly 470a can enable easy retrieval of the pad assembly from the posterior of the heart after the ablation procedure is completed. Tether assembly 470a can also serves as a physical reminder that the pad assembly is in place to reduce the probability of accidentally leaving the pad assembly in place following a surgical procedure.

FIG. 4B shows aspects of a pad assembly 400b according to embodiments of the present invention. Pad assembly 400b includes a distal portion 410b having a rounded leading edge 412b. In some cases, rounded leading edge 412b has a radius of curvature within a range from about 1 cm to about 3 cm. In some cases, rounded leading edge 412b has a radius of curvature of about 2 cm. Distal portion 410b also has a width DW, which may be within a range from about 2 cm to about 6 cm. In some cases, width DW is about 4 cm. Distal portion 410b may also have an inner width IW, between piping portions 450b, within a range from about 2.1 cm to about 4.1 cm. In some cases, width IW is about 3.1 cm. The lateral sides 420b, 430b of pad assembly 400b each present an curved shape or profile. Pad assembly 400b also includes a proximal portion 440b having a width PW, which may be within a range from about 5 cm to about 10 cm. In some cases, width PW is about 7 cm. Further, pad assembly 400b includes a piping or edge 450b that presents a rounded or cylindrical border. In some instances, piping 450b has a diameter with a range from about 0.200 inches to about 0.300 inches. In some instances, piping has a diameter of about 0.250 inches. Pad assembly 400b also has a length L, which may be within a range from about 7.25 cm to about 11.25 cm. In some cases, length L is about 9.25 cm. Overall, pad assembly 400b can be considered to present a bell shape configuration. As shown here, pad assembly 400b includes a tether transition portion 460b. Pad assembly 400b may also include a tether assembly 470b attached with a body 480b of the pad assembly via tether transition portion 460b. Tether assembly 470b can enable easy retrieval of the pad assembly from the posterior of the heart after the ablation procedure is completed. Tether assembly 470b can also serves as a physical reminder that the pad assembly is in place to reduce the probability of accidentally leaving the pad assembly in place following a surgical procedure. As compared with the pad assembly 400a shown in FIG. 4A, pad assembly 400b has a base curve portion 402b which is more rounded, a draw cord transition portion 404b which is more smoothed out and minimized, and a distal tongue portion 406b which is narrower and longer.

Figures 5A, 5B:
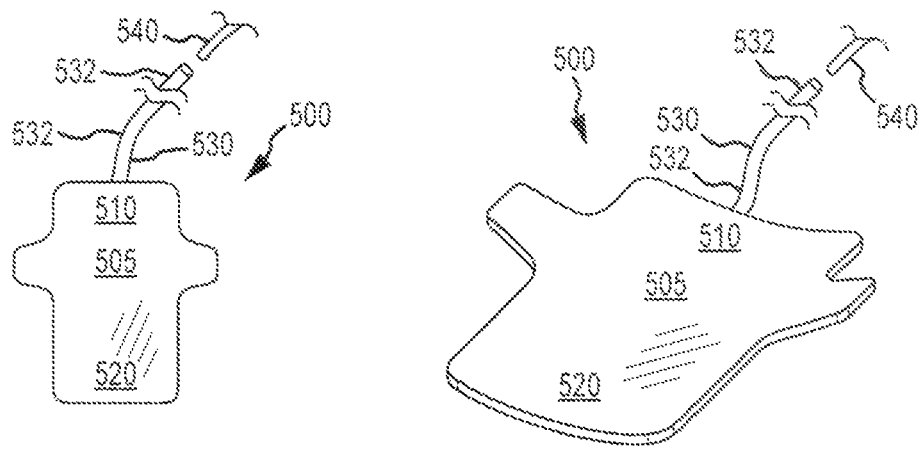
FIGS. 5A, 5B, and 5C illustrate aspects of treatment systems and methods according to embodiments of the present invention.

FIGS. 5A and 5B show aspects of a pad assembly 500 according to embodiments of the present invention. Pad assembly 500 includes a body 505 having a proximal portion 510 and a distal portion 520. Pad assembly 500 may also include a tether mechanism 530 coupled with proximal portion 510. In some instances, the tether mechanism 530 includes a tube 532, and is adhesively bonded to the pad body 505. Pad assembly 500 may further include or be operated in conjunction with a stylet mechanism 540. For example, stylet mechanism 540 may be inserted into tube 532 by a physician or operator. In this way, the physician or operator can use the stylet mechanism 540, as it resides within or is received by the tube 532, to help push or maneuver the pad assembly 500 into a desired position within the patient anatomy. At or toward the end of the treatment procedure, the surgeon may pull on the tether mechanism, thus enabling an easy and safe removal of the pad assembly from the patient's body.

Figure 5C:
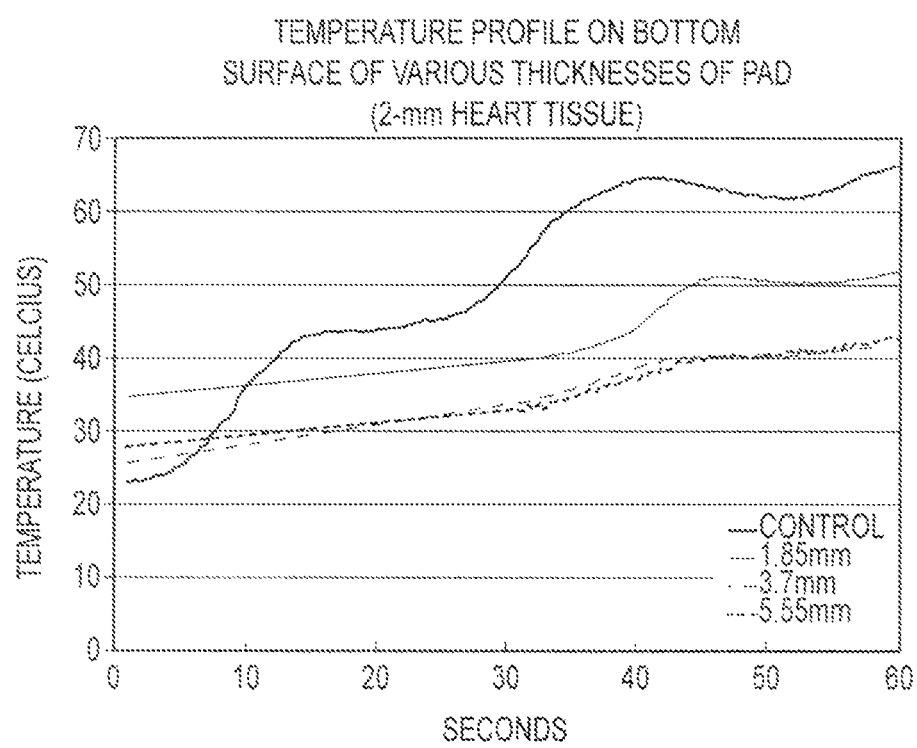

FIG. 5C illustrates exemplary relationships between tissue temperature and pad assembly body thickness. As depicted here, in a control example with no pad body disposed between the atrial wall (of 2 mm thickness) and the pericardium or esophagus, the temperature of the pericardium or esophagus continues to rise as ablation current is applied to the atrial wall over the course of about 60 seconds, reaching 50° C. at about 30 seconds. In comparison, when using a pad assembly having a body thickness of 1.85 mm, the temperature of the pericardium or esophagus rises more slowly, reaching 50° C. at about 45 seconds. And when using a pad assembly having a body thickness of 3.7 mm or 5.55 mm, the temperature of the pericardium or esophagus rises even more slowly, and does not reach a temperature of 50° C. within 60 seconds.

In some embodiments, the pad assembly or the body of the pad assembly has a generally planar thickness. For example, the thickness can be within a range from about 1 mm to about 6 mm. In some instances, the thickness of the pad assembly or body is about twice as thick (e.g. 6-8 mm) at the center as its width near the edges of the assembly or body. Such variation in thickness has been found to facilitate the ease with which the pad assembly is placed between the pulmonary veins while providing a very non-traumatic interface with the structures contacting the edges of the pad assembly, such as the pulmonary veins (PV) and the pericardial reflection 620 near the transverse sinus 630 shown in FIG. 6, which illustrates an anterior view of the heart, as viewed through the front ribs or sternum. The proximity of the posterior atrial wall 650 and the esophagus is illustrated by the presence of the esophageal prominence. A pad assembly can be placed anterior to the pericardium, between the posterior left atrium or atrial wall and the pericardium.

Figure 6:
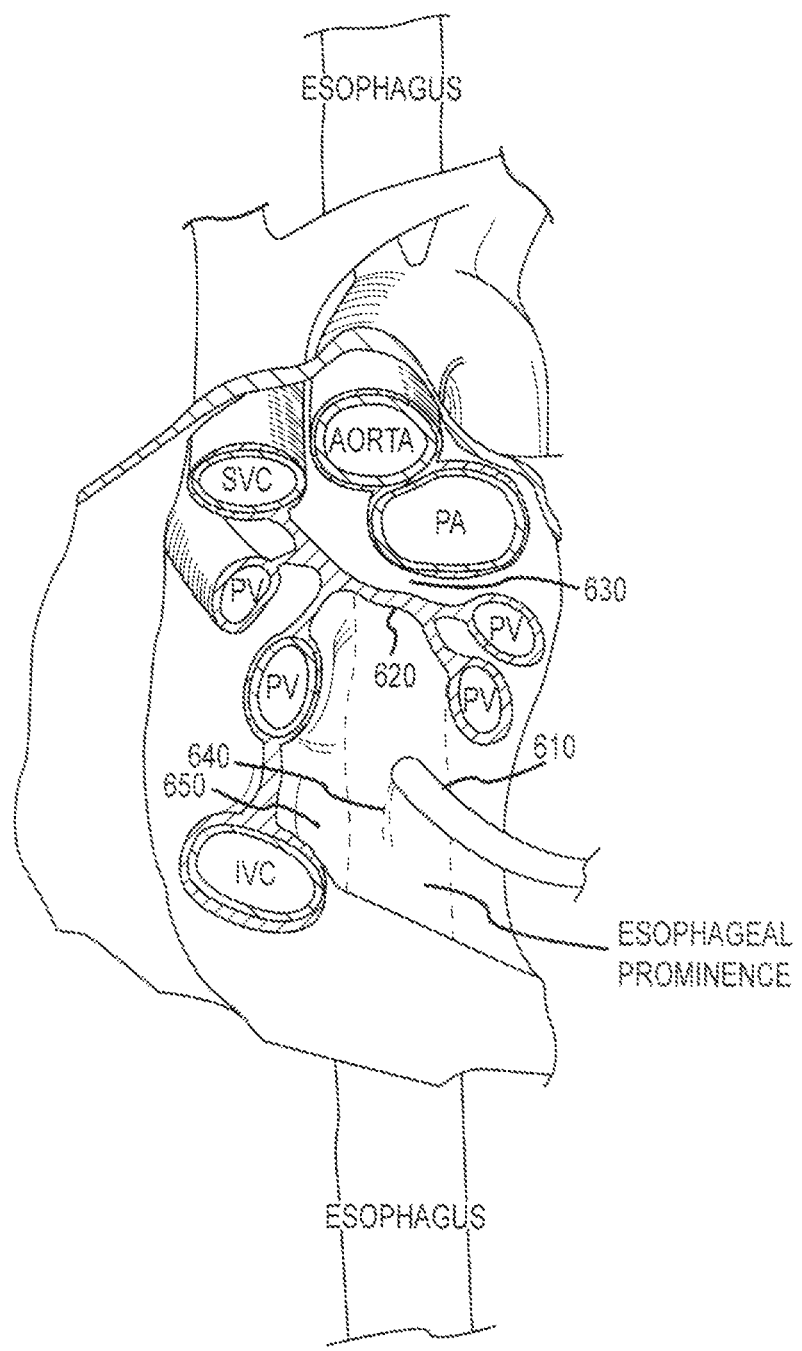
FIG. 6 illustrates aspects of treatment systems and methods according to embodiments of the present invention.

As shown in FIG. 6, a probe assembly 610 such as a monopolar probe can be placed within an interior chamber of the heart. A pad assembly can be placed posterior to the heart and anterior to the esophagus. A pericardial reflection is typically present between the right and left pulmonary veins. The process of ablating between the right and left pulmonary veins, for example as illustrated by lesion or ablation pattern 640, may involve a concomitant dissection of the pericardial reflection between the right and left pulmonary veins at or near the epicardium. The pericardial reflection presents a ridge or line of attachment between the right and left pulmonary veins. For example, FIG. 6 illustrates a pericardial reflection between the right pericardial veins and the left pericardial veins. A transverse pericardial sinus 630 is disposed near the pericardial reflection 620 and pulmonary artery (PA). Due to the close apposition between the esophagus and the posterior left atrial (LA) wall, between the left- and right-sided pulmonary veins, by placing the pad assembly between the esophagus and atrial wall, it is possible to protect the esophagus while delivering ablative energy to the posterior aspect or wall of the left atrium during cardiac AF treatments.

When current is delivered by way of the ablation electrode placed inside of the heart, current and temperature is transmitted through the atrial wall, which may be between about 2 mm and about 6 mm thick, the current can propagated from the atrial wall directly into the assembly pad, thus creating a narrow and well defined lesion in the atrial wall, which is achieved by the narrow and well defined current path afforded by the pad assembly. Embodiments of the present invention provide systems and methods for performing any of a variety of lesions or lesion sets on heart tissue. For example, embodiments encompass the performance of a posterior left atrial connection (PLAC) between 2 PV-encircling ablations epicardially. Embodiments may also encompass the performance of left atrial ablations. Embodiments also encompass the creation of any of the lesions sets described in U.S. patent application Ser. Nos. 12/124,743 and 12/124,766 filed May 21, 2008, the disclosures of which are incorporated herein by reference.

In addition to protecting esophageal tissue, pad assemblies can be used to protect any of a variety of patient tissue in situations where target tissue is ablated and it is desirable to protect other tissue adjacent to the ablated tissue. For example, tumors in the prostrate, kidney, liver, and lung can be heated to kill all or most cells in the tumor. Often those tumors are adjacent to other organs, blood vessels, and other anatomical features that should be protected to the extent possible. By providing a current sink mechanism such as a pad assembly at or near the target tissue, it is possible to reduce current dispersal in the patient, and in turn minimize unwanted direct heating effects which unsinked current may otherwise produce.

According to some embodiments, the pad assembly or a portion thereof may include a material having an electrical conductivity value that is equal to or greater than the electrical conductivity value of the atrial wall or target tissue. Hence, current can flow from the target tissue into the pad assembly, instead of spreading out into other areas of the target tissue or patient anatomy. In this way, it is possible to prevent or inhibit unwanted conductive heating of the esophagus or other tissue which may lead to thermal injury. In some cases, the bulk material of the pad assembly or body is an electrical semiconductor with a volume resistivity as measured at about 1 MHz of about 2-2000 ohm-cm. The pad assembly can operate to prevent or inhibit potential damage to the esophagus and to other non-cardiac tissue. In some exemplary embodiments, the pad assembly is a standalone device that protects non-cardiac tissues from thermal damage while interfering minimally with the current fields that enable reliable creation of lesions in the heart during ablation. In some embodiments, a metallic return electrode is molded within the pad body to serve as a return path for ablation currents applied by an endocardial surgical ablation probe. In some cases, the pad body may include a polymeric material. Such embodiments can enhance the effect of the ablation to the posterior part of the atrium because current may not spread as much as it would otherwise, for example as in cases where a return electrode is placed on the patient's skin. In some cases, the pad assembly can be used in conjunction with a return patch or pad that is placed on the patient's skin, and the pad assembly is not electrically connected via a return path to an electrosurgical unit (ESU).

Electrically insulative polymers provide one class of materials appropriate for use in manufacturing the pad assembly or body. Additives may be included with the base polymers so as to create mixtures that can be cast molded or extruded into structures that are electrically semiconducting and thermally insulating. Silicone and polyurethane are exemplary selections for use as the base polymer, and other base polymers could work as well. Carbon powders or carbon strands are exemplary additives which can be included with base material to create finished parts with electrical resistivity values in a desired range. Metallic additives can be used as well. In some exemplary embodiments, carbon materials are used because many metals are much more thermally conductive than the type of carbon materials that can be used for these additives. In exemplary embodiments, the pad assembly is constructed of or coated with biocompatible materials. Hence, base polymers can be compounded to achieve desired electrical and thermal conductivity values.

Hydrogels are another class of materials that could be used, with salts incorporated into the hydrogel to form electrical semiconducting structures. In some embodiments, salts rather than water can be used to hydrate a structure that is initially or commercially provided in a dehydrated from. Higher salt content in the hydrating fluid can provide a hydrogel structure with higher electrical conductivity after the hydration process is complete, according to some embodiments.

Pad assemblies can be constructed of materials having desired flexibility and firmness parameters, which can enhance the safety of the device and the ease in which it may be properly placed within the patient's anatomy. In some cases, polyurethane or silicone base materials can be used. Materials with a 40 A-80 A shore hardness can provide a device that is easy to place, and that is soft enough to reduce the probability of tearing critical structures like the pulmonary veins.

In some cases, the pad assembly or body can be configured to appear translucent under fluoroscopy. That is, the location of the pad assembly can be readily observed, but the pad is not so radio-opaque that it interferes with imaging of other structures in the fluoroscopic view. Additives such as barium which add radiographic density without having a significant effect on electrical or thermal conductivity can be added to the mixtures to provide this feature of the pad.

Pad assemblies may include material having an electrical conductivity that is less than the conductivity of normal saline (0.9% weight/volume) and greater than or equal to the conductivity of the target tissue. Exemplary pad assembly material may also be thermally insulative. In some cases, pad assemblies include a biocompatible high frequency emf or EMI filter material.

Pad assemblies may include material having a thermal conductivity value that is within a range from about 0.05 W/m° C. to about 1.0 W/m° C. Due to the electrical and thermal conductivity properties of the pad assembly, ablative current can be applied to target tissue such as the posterior atrial wall without inducing high or damaging levels of direct heating in other tissue such as the esophagus. The thermal insulating properties of the pad assembly can, for example, protect the esophagus so that heat which is at the epicardial surface of the left atrium does not thermally conduct so much that the esophagus tissue becomes excessively hot (e.g. above 50° C.). At the same time, target tissue such as the left atrial wall is sufficiently or completely heated, so as to produce a transmural lesion.

Cadaver Experiments

Two cadaver specimens were used to study the material performance, geometry and fit, and surgical delivery aspects of exemplary pad assembly or IsoPad constructions. Specimen 1 was a 120 lb, 64" female. Specimen 2 was a 180 lb, 70" male.

The pad assembly or body was constructed with an electrically conductive and thermally insulative material obtained from NuSil Technology LLC, Carpinteria, Calif. It was observed that the pad material provided exceptional lesions in both male and female cadavers wherewith the atrial tissue thickness varied between 2 and 6 mm. Transmural lesions were created through atrial tissue in all cases, but pericardium underneath the atrial tissue was only protected when a pad assembly was used. In contrast, pericardium over the esophagus was ablated when the pad assembly was not used during ablation of the atrial wall.

Figure 7A:
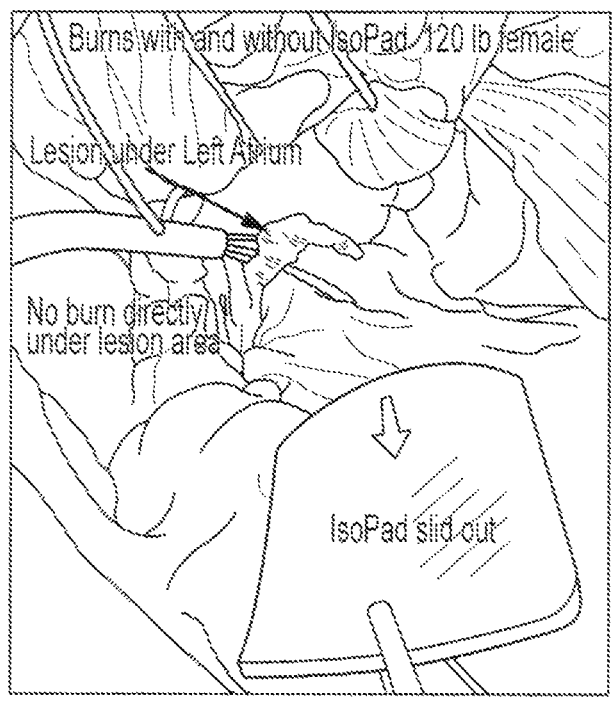
Figure 7B:
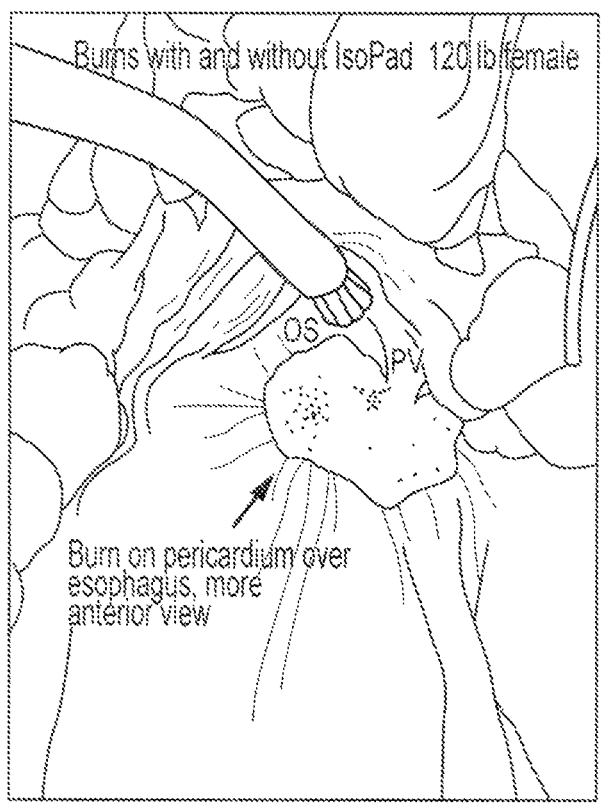
Figure 7C:
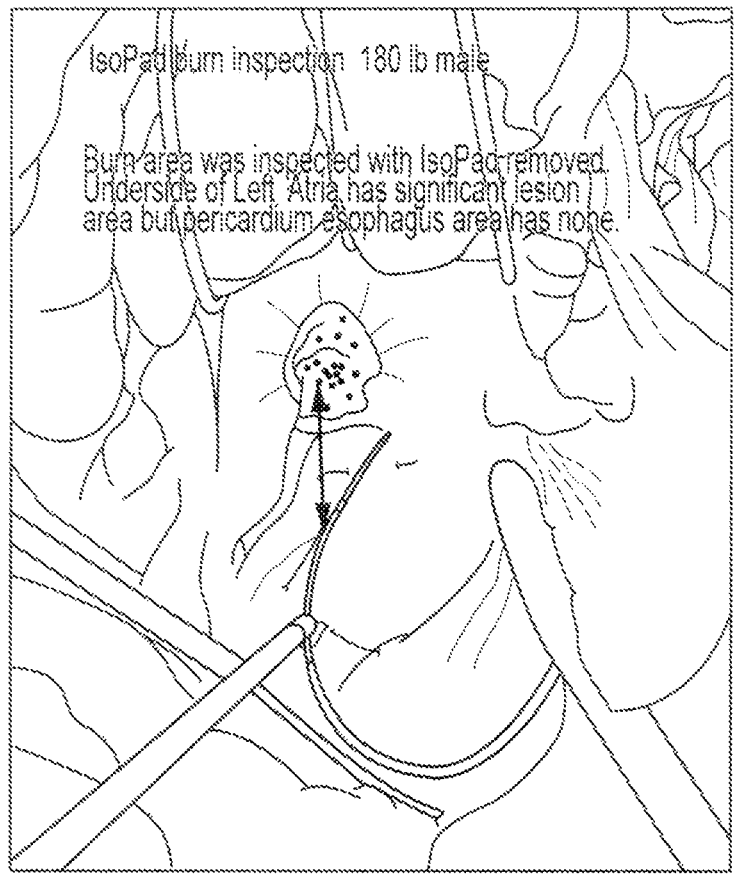

Specifically, FIGS. 7A and 7B show the protective effect of the pad assembly in the female specimen, and FIG. 7C shows the protective effect of the pad assembly in the male specimen. As illustrated in FIG. 7A, there is a lesion under the left atrium, and there is no burn directly under the lesion area. In contrast, FIGS. 7B and 7B1 indicate that when ablation is performed without the presence of a pad assembly between the atrial wall and the pericardium and esophagus, there is a distinct burned area on the pericardium over the esophagus. FIG. 7C shows inspection of the burn area with the pad assembly removed. As depicted here, the underside of the left atria has a significant lesion area, and the pericardium/esophagus area has none. The treatment protocol in this study was performed with two ablations at 70 C, 60 s, 30 W/e.

Temperature probing during ablation showed that with use of the pad assembly, the temperature at the pericardial surface posterior to the left atrium was well below 50° C., further confirming that the pad assembly material provided safety to the esophagus.

Figure 8A:
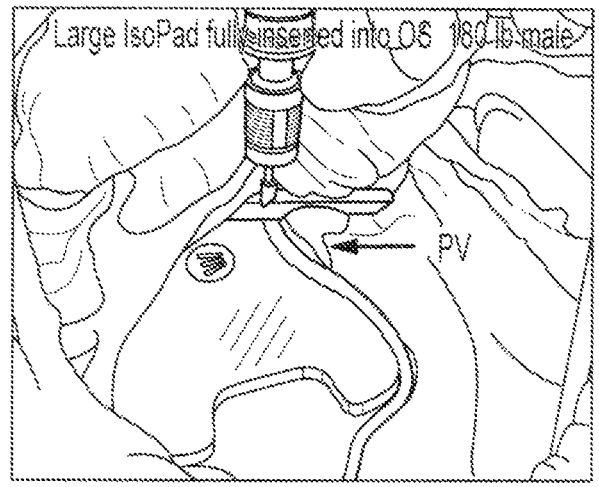
FIGS. 8A and 8B illustrate aspects of treatment systems and methods according to embodiments of the present invention.
Figure 8B:
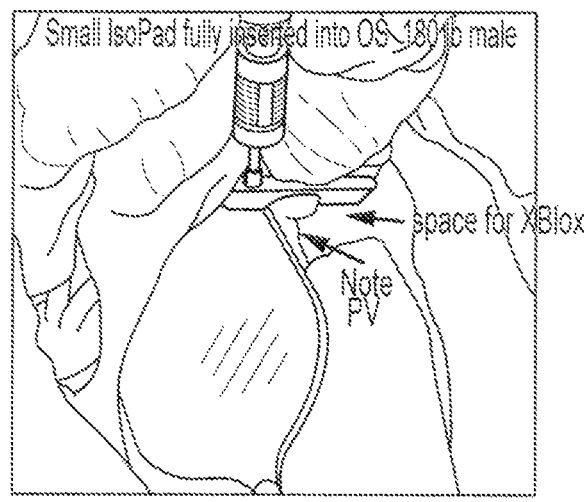

Two pad assembly geometries were tested during this cadaver study. The first pad assembly included an oval-shaped configuration such as that depicted in FIG. 3. The second pad assembly included a bell-shaped configuration such as that depicted in FIG. 4. It was observed that the bell-shaped configuration provided certain benefits related to performance and the ability to deploy the pad assembly inside the human anatomy. With regard to placing or maneuvering the pad assembly into the space between the pulmonary veins, it was observed that both shapes performed equally well. With regard to maintaining a fully tucked position in between the pulmonary veins and up against the pericardial reflection, the bell-shape configuration was observed to provide an added benefit of staying put and not shifting side-to-side in the oblique sinus, whereas the oval-shaped configuration was not observed to have sufficient extended material to anchor the pad in place against surrounding structures. FIG. 8A depicts a fully tucked position of an assembly pad having a bell-shaped configuration. FIG. 8B depicts a fully tucked position of an assembly pad having an oval-shaped configuration.

Figure 9A:
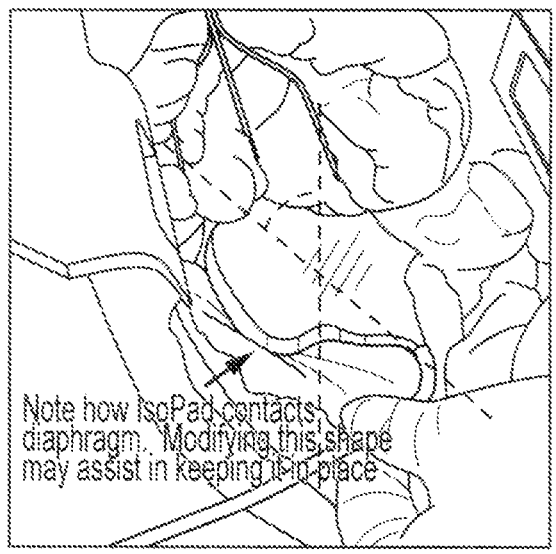
FIGS. 9A and 9B depict aspects of treatment systems and methods according to embodiments of the present invention.
Figure 9B:
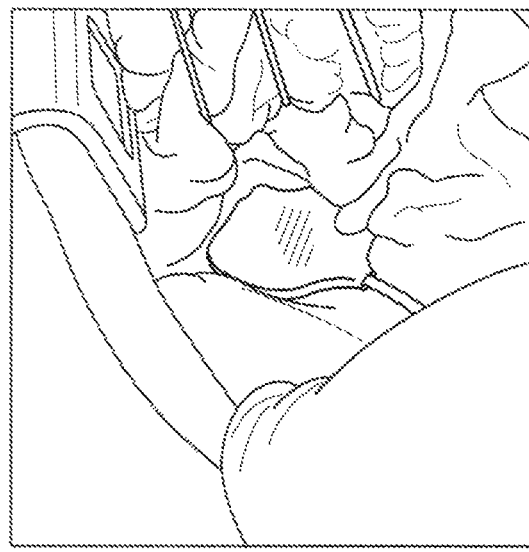

Relatedly, in some instances the oval-shaped configuration exhibited more of a tendency to slide backward away from the PV pocket, as compared with the bell-shaped configuration. Both configurations also exhibited an angled fit form the sagittal plane axis. For example, as shown in FIGS. 9A and 9B, respectively, it was observed that with both the oval-shaped and bell-shaped configurations, when fully inserted, a central longitudinal axis of the pad assembly or pad body rests at nearly a 45° angle from the sagittal plane axis or left ventricle.

Figure 10:
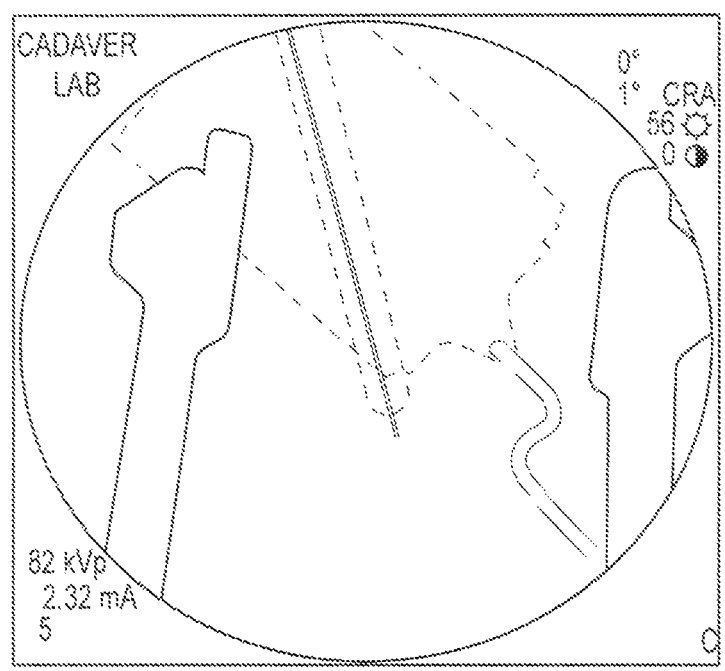
FIG. 10 shows aspects of treatment systems and methods according to embodiments of the present invention.

Regarding the material hardness of the pad assemblies, it was observed that out of two samples (50 A and 65 A durometer), the harder durometer exhibited enhanced performance because it was less likely to buckle when being pushed into the target space (e.g. between the pulmonary veins). Regarding the radiopacity of the pad assemblies, the configuration was tested for radiopacity using a standard C-arm and was found to lack significant opacity, as indicated in FIG. 10.

Plaster of Paris was cast into both specimens for future study. Castings were successful and showed that there can be a significant difference in the widths of the left and right PV spacing between smaller and larger patients. The larger, male specimen had a spacing of about 50-55 mm between the right PVs and the left PVs, whereas the smaller, female specimen had a spacing of about 30-35 mm between the right PVs and the left PVs.

The material used for constructing the pad assembly or pad body was observed to provide desirable conductivity properties, as confirmed by both bench testing and cadaver specimen testing. The overall geometry of the pad assemblies were observed to provide suitable overall dimensions to fit in comfortably yet snuggly inside the PV pocket between the right PVs and the left PVs. In some instances, the bell-shaped configuration was observed to exhibit beneficial properties, related to stabilization of the pad by utilizing adjacent tissue structures to hold it in place and prevent it from shifting side-to-side and ultimately sliding backwards and out of the PV pocket. Additional design configuration features can help to prevent unwanted movement of the pad assembly. For example, a stiff ripcord coupled with the pad assembly or pad body can help keep the pad assembly in place. The ripcord can be clipped to the chest wall and can provide a compressive force that can help prevent or inhibit the pad from slipping out of the PV pocket. Relatedly, a suction mechanism can be coupled with or integrated into the pad assembly or pad body. The suction mechanism can operate to adhere the pad assembly or body with the patient's pericardial surface, which can help prevent or inhibit the pad assembly from slipping out of the PV pocket. Further, stipples or a friction mechanism can be coupled with or integrated into the pad assembly or pad body. The stipples or friction mechanism can help to create or enhance friction between the pad assembly and the patient's tissue.

In some cases, material of the pad assembly or pad body can include barium sulfate, which can provide or increase the opacity of the pad assembly. In some case, material of the pad assembly or pad body can include components which confer increased or desired durometer values to the pad assembly. By providing pad assemblies with desired durometer values, it is possible to prevent or inhibit buckling of the pad assembly upon insertion to the surgical site.

In sum, the cadaver lab working example confirmed aspects of certain properties of the pad assemblies, including the material, geometry, hardness, radiopacity, and feasibility of implementing a pad assembly in the human anatomy.

Figure 11:
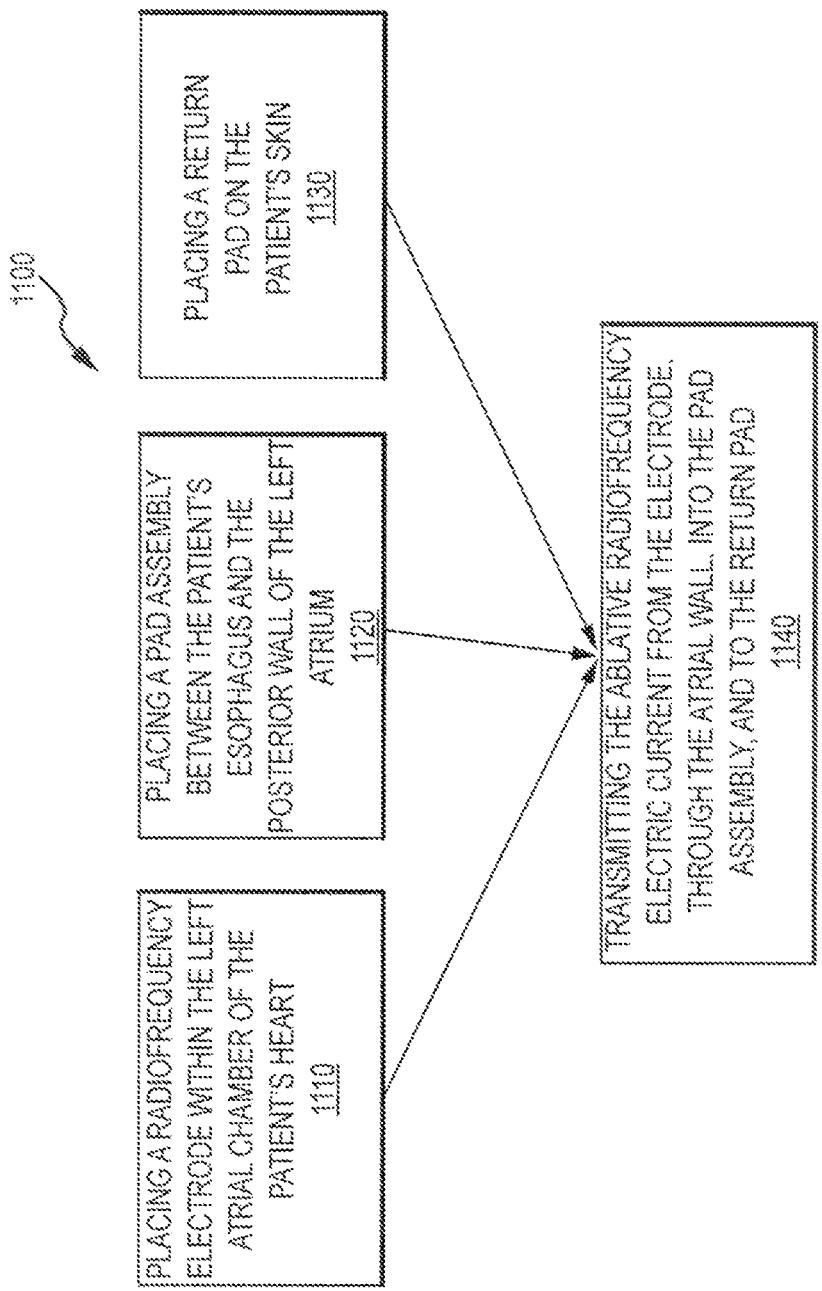
FIG. 11 shows aspects of treatment methods according to embodiments of the present invention.
Figure 12:
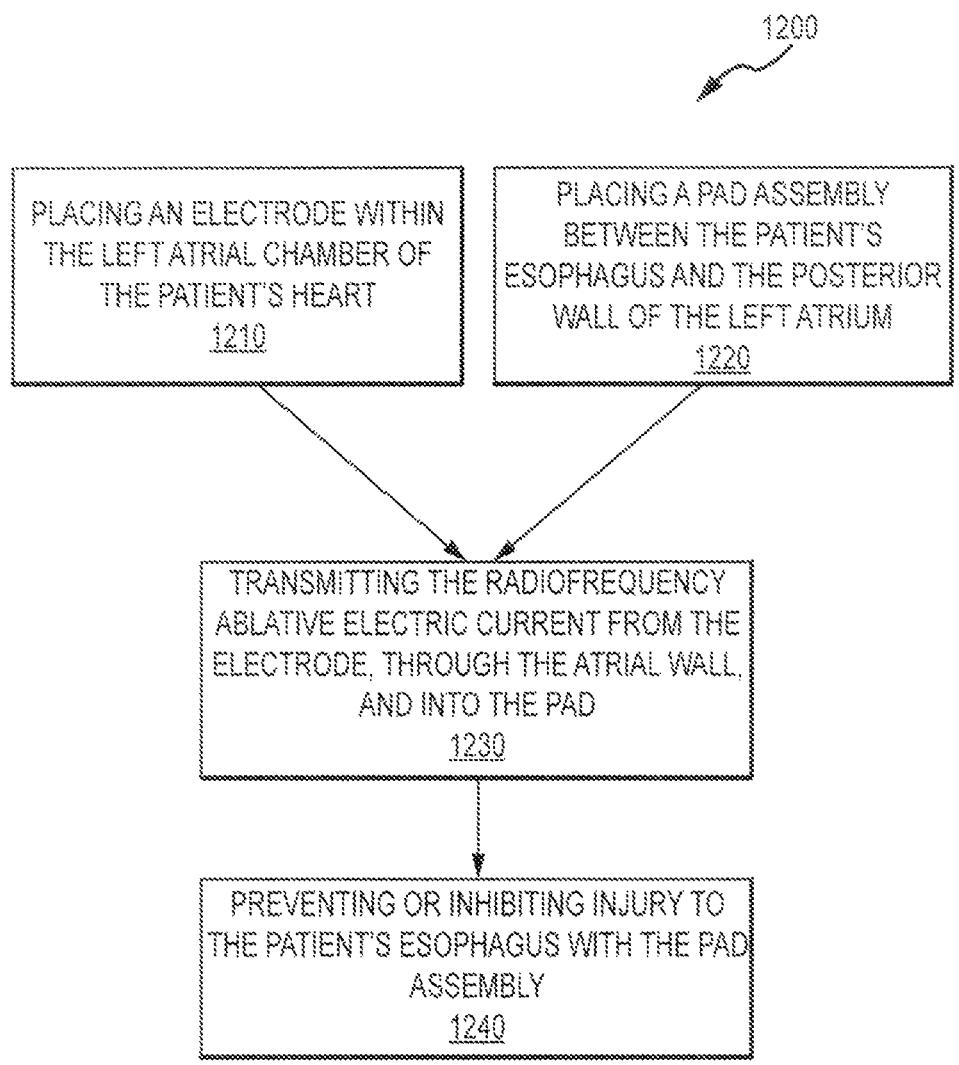
FIG. 12 shows aspects of treatment methods according to embodiments of the present invention.
Figure 13:
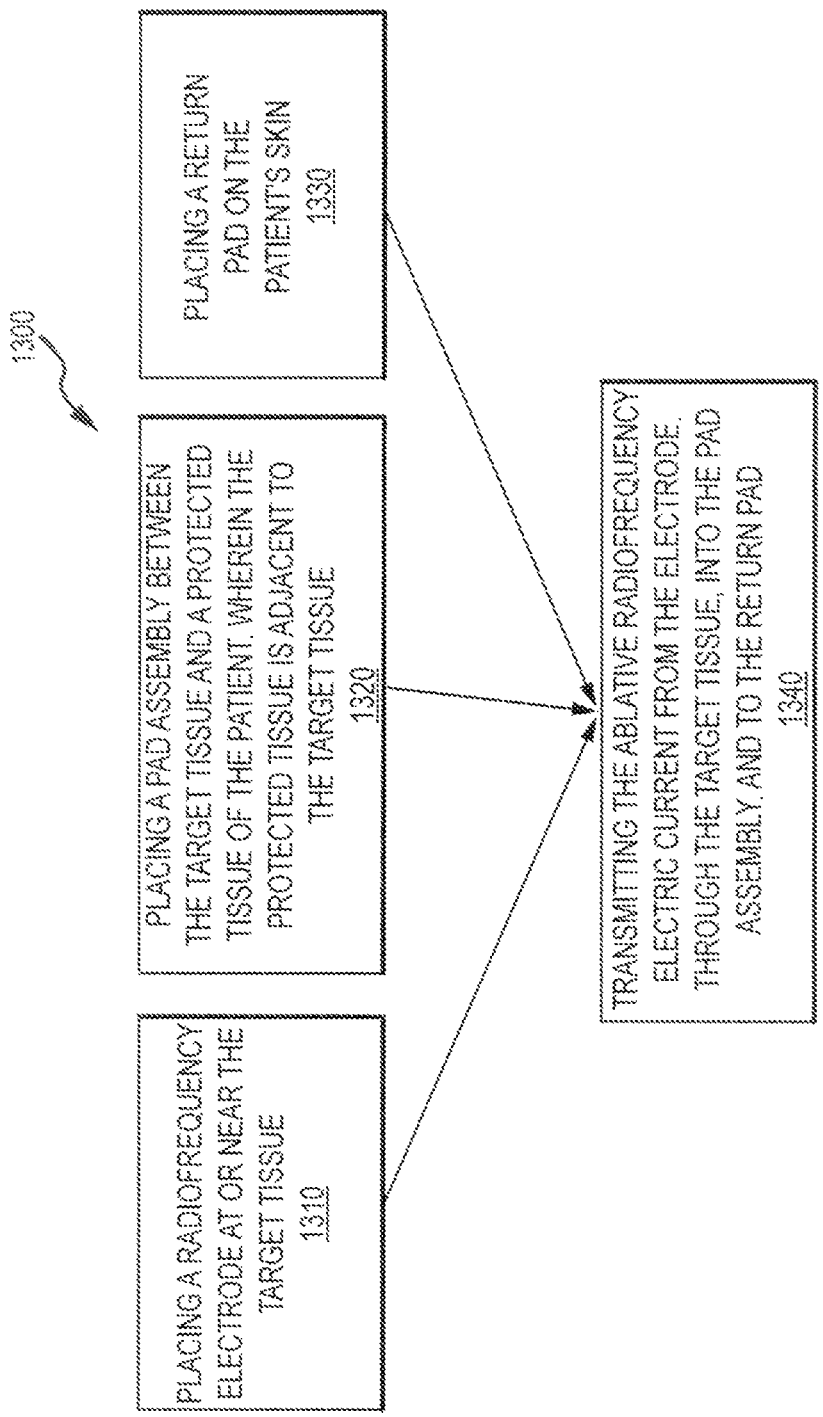
FIG. 13 shows aspects of treatment methods according to embodiments of the present invention.
Figure 14:
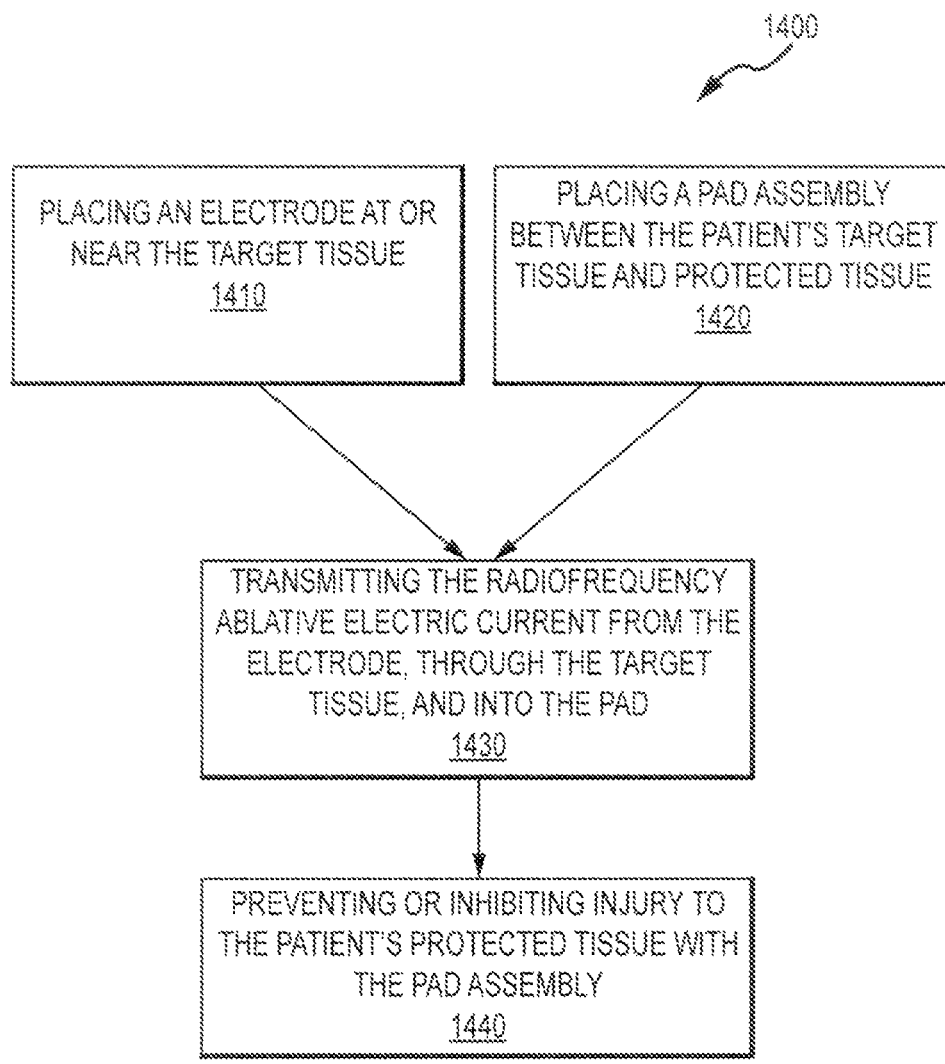
FIG. 14 shows aspects of treatment methods according to embodiments of the present invention.

FIGS. 11-14 illustrate exemplary procedural aspects associated with various method embodiments of the present invention. FIG. 11 shows illustrative steps of a method 1100 for delivering an ablative radiofrequency electric current through a posterior wall of a patient's left atrium. As shown here, method 1100 includes a step 1110 of placing a radiofrequency electrode within the left atrial chamber of the patient's heart, a step 1120 of placing a pad assembly between the patient's esophagus and the posterior wall of the left atrium, a step 1130 of placing a return pad on the patient' skin, and a step 1140 of transmitting the ablative radiofrequency electric current from the electrode, through the atrial wall, into the pad assembly, and to the return pad. FIG. 12 shows illustrative steps of a method for preventing or inhibiting injury to a patient's esophagus during delivery of an ablative current through a posterior wall of the patient's left atrium. As shown here, method 1200 includes a step 1210 of placing an electrode within the left atrial chamber of the patient's heart, a step 1220 of placing a pad assembly between the patient's esophagus and the posterior wall of the left atrium, a step 1230 of transmitting the radiofrequency ablative electric current from the electrode, through the atrial wall, and into the pad, and a step 1240 of preventing or inhibiting injury to the patient's esophagus with the pad assembly. FIG. 13 shows illustrative steps of a method for delivering an ablative radiofrequency electric current through a target tissue of a patient. As shown here, method 1300 includes a step 1310 of placing a radiofrequency electrode at or near the target tissue, a step 1320 of placing a pad assembly between the target tissue and a protected tissue of the patient, wherein the protected tissue is adjacent to the target tissue, a step 1330 of placing a return pad on the patient' skin, and a step 1340 of transmitting the ablative radiofrequency electric current from the electrode, through the target tissue, into the pad assembly, and to the return pad. FIG. 14 shows illustrative steps of a method for preventing or inhibiting injury to a protected tissue of a patient during delivery of an ablative current through a target tissue of the patient. As shown here, method 1400 includes a step 1410 of placing an electrode at or near the target tissue, a step 1420 of placing a pad assembly between the patient's target tissue and protected tissue, a step 1430 of transmitting the radiofrequency ablative electric current from the electrode, through the target tissue, and into the pad, and a step 1440 of preventing or inhibiting injury to the patient's protected tissue with the pad assembly.

Figure 15:
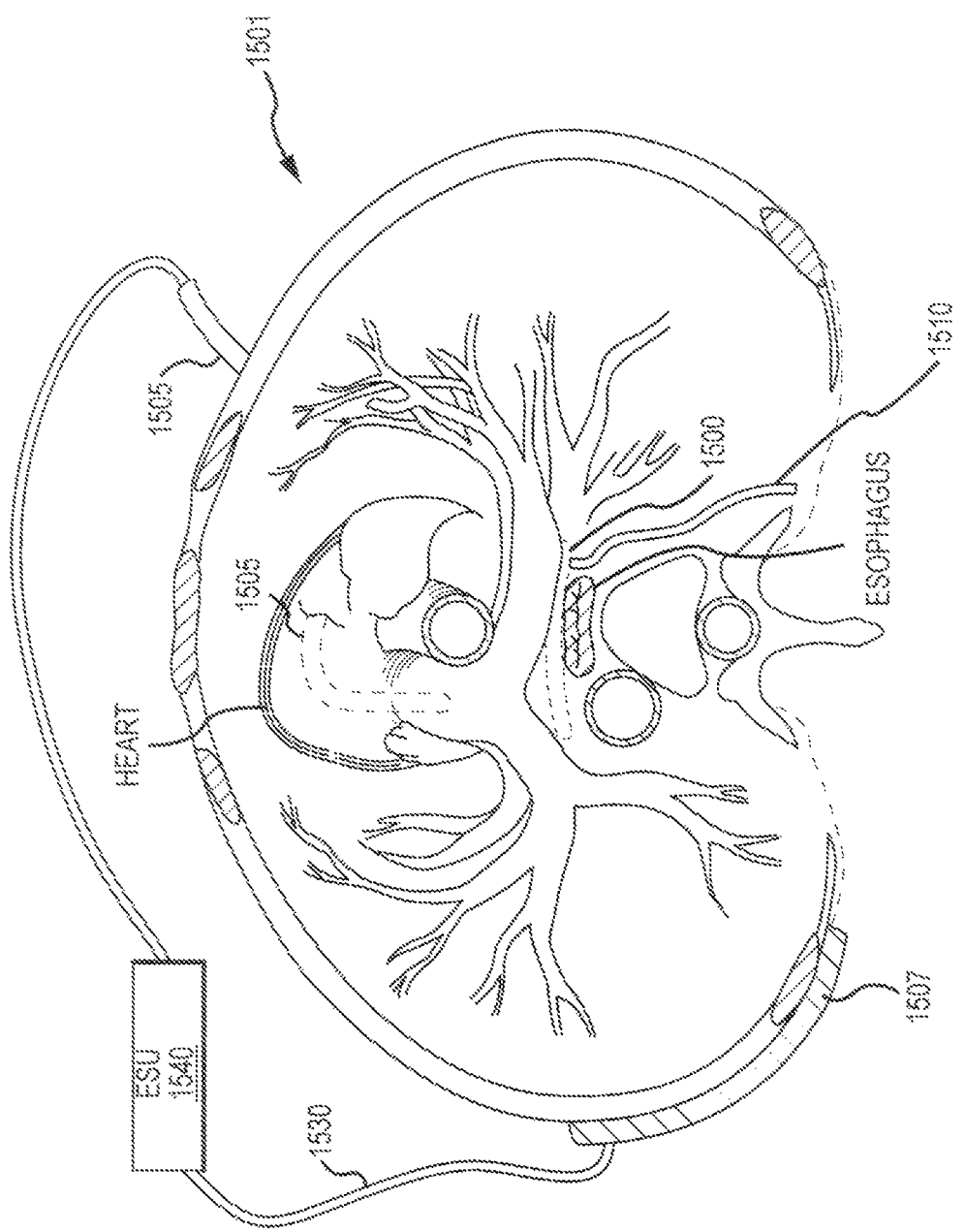
FIG. 15 illustrates aspects of treatment systems and methods according to embodiments of the present invention.

FIG. 15 illustrates a top view of a transverse section of a patient 1501. As shown here, a pad assembly 1500 can be positioned anterior to the esophagus and posterior to the heart, for example in the pericardial space. In some instances, pad assembly 1500 can be shaped to fit in the pericardial space and conform to the posterior portion of the left atrium and right atrium. FIG. 15 also depicts an ablation probe 1505 disposed within an interior chamber of the heart, and a return pad 1507 disposed exterior of the patient's body, for example on the surface of the patient's skin. Ablation probe 1505 and return pad 1507 can be operatively coupled with an Electrical Surgical Unit (ESU) 1540. In some cases, pad assembly 1500 is configured for placement between the patient's esophagus and the posterior wall of the patient's left atrium, and operates to receive ablative radiofrequency electric current transmitted by an electrode of the ablation probe. Relatedly, return pad 1507 is configured in operative association with the electrosurgical unit assembly, and receives the ablative radiofrequency electric current delivered from the pad assembly. The posterior wall of the left atrium can have an electrical conductivity value, and the pad assembly can include a material having an electrical conductivity value that is equal to or greater than the electrical conductivity value of the posterior wall of the left atrium. In some case, the electrical conductivity value of the material is within a range from about 20 (ohm-cm) to about 500 (ohm-cm). In some cases, the material has a thermal conductivity value that is within a range from about 0.05 W/m° C. to about W/m° C. In some cases, the pad assembly includes an anterior portion material having an electrical conductivity value within a range from about 20 ohm-cm to about 500 ohm-cm coupled with a posterior portion material having a thermal conductivity value that is within a range from about 0.05 W/m° C. to about 1.0 W/m° C. In some cases, the pad assembly is positionable between epicardial tissue and pericardial tissue of patient's heart. As shown here, the pad assembly may include or be coupled with a tether mechanism 1510. In some cases, the pad assembly includes an anterior portion and a posterior portion, and is positionable between the patient's atrial wall and esophagus so that the anterior portion faces toward the atrial wall and the posterior portion faces toward the esophagus. Return pad 1507 can be electrically coupled with a thin flexible cable 1530 that connects to an Electrical Surgical Unit (ESU) 1540 to return current originating from the ablation device or probe. In such embodiments, the anterior portion of the pad assembly facing the atrial wall is preferably more electrically conductive than the posterior potion to further increase current flow through the atrial wall to improve atrial wall ablation and to decrease current flow through the posterior portion to further decease potential heating of the esophagus. Pad assembly 1500 can operate to prevent or inhibit potential damage to the esophagus and to other non-cardiac tissue. ESU 1540 can be configured to provide power control using standard power delivery algorithms. Typically, the ESU is configured to operate in a stable matter during ablation procedures involving any of a variety of tissue types having different degrees of thermal capacity.

An exemplary surgical procedure may include opening the pericardium, inserting the pad assembly 1500 along the posterior aspect of the left ventricle, and advancing the pad assembly adjacent the right coronary to position the pad assembly posterior to the heart, for example posterior to the left atrial appendage.

A surgeon may use a pad assembly and ablation provide during a treatment procedure in which the left atrium is open. For example, a cardiopulmonary bypass technique can be used to remove blood from the heart, and an ablation probe device 1505, which may include a monopolar probe, can be inserted within the heart chamber. Optionally, the surgeon may use a visualization device as an aid in positioning the ablation probe or pad assembly. In some cases, the surgeon may view or evaluate the heart tissue curvature or contour, and bend or form the ablation electrode device to provide a corresponding curvature or contour in the device. The surgeon may then contact the atrial wall or tissue with the formed device. According to some embodiments, the pad assembly is placed within the pericardial space, between the pericardium and the heart, and ablations are performed in the left atrium. During the ablation procedure, the ablation probe can be moved and positioned within the heart chamber and relative to the pad assembly, as desired. Hence, the pad assembly can be placed near the posterior part of atrium, and the probe device can be moved independent of the pad assembly. In this way, the surgeon is free to create lesions at any of a variety of locations, such as at or near the mitral valve annulus, which may otherwise be difficult using some known bipolar clamping devices.

Typically, a pad assembly configured to be connected to an ESU includes a conductive mechanism which is much more conductive than the patient tissue, and behaves like an isopotential surface. When the ablation probe electrode is positioned directly across from the pad assembly, the ablation probe device and return pad assembly combination can operate in a fashion similar to that of a bipolar ablation system, with current remaining within a constrained region, passing from the ablation probe, directly through the tissue, and to the pad assembly. When the ablation probe electrode and pad assembly are positioned at a further distance from one another, the ablation probe device and return pad assembly combination can operate in a fashion similar to that of a monopolar ablation system, where the current traveling from the ablation probe and spreading out in all directions, with current density (and heating rate) decreasing rapidly as a function of distance from the ablation probe. Put another way, as the distance between the ablation electrode and the pad assembly becomes greater, there is a corresponding transition from a bipolar lesioning configuration to a monopolar lesioning configuration. Relatedly, the heat generated is proportional to the square of the current. Hence, if a current is distributed in a way to provide 10% of an original amount of current, the resulting rate of heat generation will be about 1% of original rate of heating. As noted elsewhere herein, the indifferent pad assembly can operate to prevent or inhibit noncardiac tissue, such as the esophagus, from being damaged during an ablation procedure.

In some cases, tissue positioned between the pad assembly and the ablation electrode may provide minimal or nominal resistance. For example, a tissue such as the atrial wall may provide about 10 ohms of resistance. Relatedly, certain ESU devices may not operate effectively in low resistance circumstances. For example, ESU devices may not operate as desired when the resistance is less than about 25 ohms. With continued reference to FIG. 2, in some embodiments pad assembly 200 may include one or more noninductive power resistors 260 in operative association with the return lines. As shown here, the pad assembly can include two return lines, and each of these lines may include two noninductive power resistors 260. Each of the resistors may provide, for example, between about 10 and about 50 ohms of resistance. In some cases, the pad assembly 200 is configured to allow up to 2 amps of current equally distributed in each of two return lines.

An ESU can be configured to monitor return current separately from two return paths. If the current exceeds a predetermined threshold, the ESU may be configured to automatically reduce or terminate power delivery.

Figure 15A:
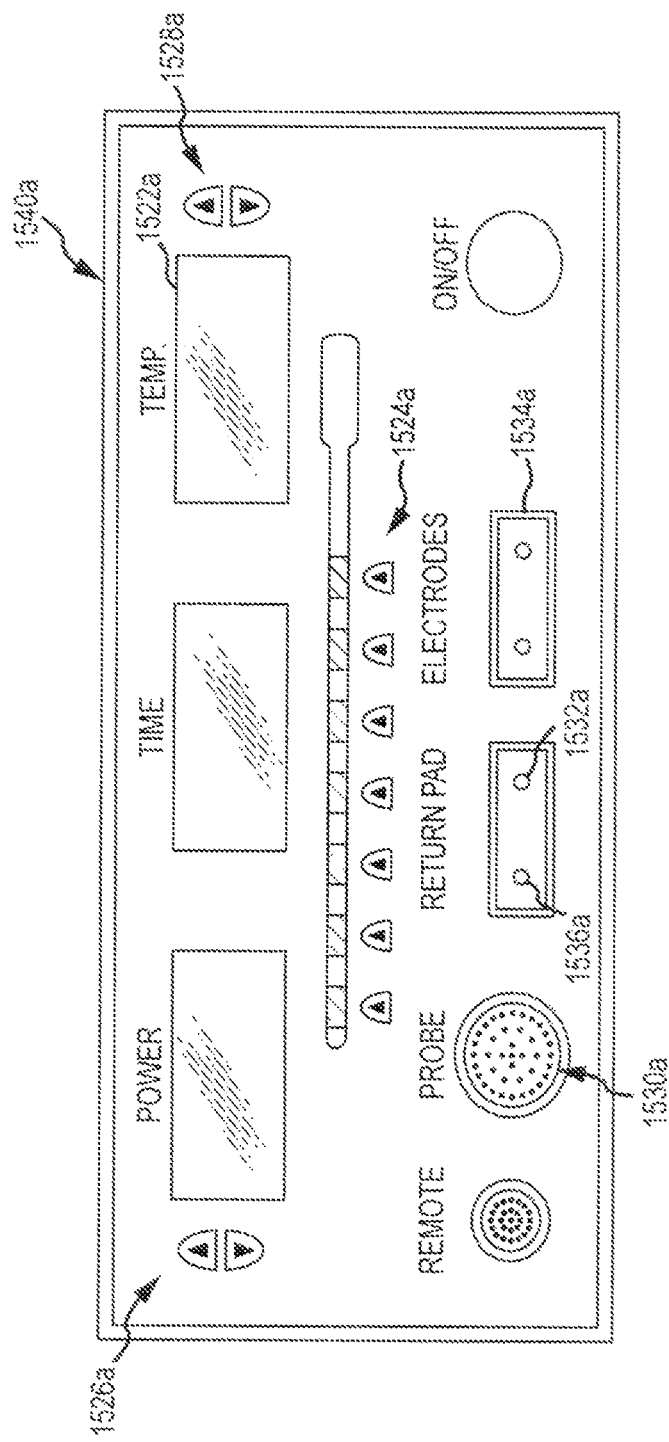
FIG. 15A illustrates aspects of treatment systems and methods according to embodiments of the present invention.

Pad assemblies can be used in conjunction with an electrosurgical unit (ESU) such as the ESU 1540a shown in FIG. 15A. ESU 1540a can be used to supply and control power to a surgical probe or other electrophysiological device, and may include a plurality of displays 1522a, as well as buttons 1524a, 1526a and 1528a that are respectively used to control which of the electrodes on the probe or electrophysiological device receive power, the level of power supplied to the probe or electrodes, and the temperature at the probe or electrodes. Power is supplied to the surgical probe or other electrophysiological device by way of a power output connector 1530a. Lesion creation procedures sometimes require that up to 2 amperes be returned to the ESU 1540a and, to that end, a pad assembly that can handle up to 2 amperes can be placed within the patient's body and connected with the ESU. A return pad can be connected to a pair of power return connectors 1532a and 1534a on the ESU 1540a. The power return connectors 1532a and 1534a in the exemplary ESU 1540a illustrated in FIG. 15A has a rectangular profile and recessed male pins 1536a, while the power output connector 1530a has a circular profile. In order to mate with the rectangular power return connectors 1532a and 1534a, a connector of the return pad may include a mating portion with a rectangular profile and longitudinally extending female pin-connects. The profile need not be perfectly rectangular so long as the profile substantially corresponds to that of the power return connectors 1532a and 1534a. For example, the middle of the top and bottom surfaces of mating portion may include longitudinally extending grooves for mechanical keying with the corresponding connector. The shape and style of the power return connectors 1532a and 1534a and the corresponding mating portion on the connector need not be rectangular. However, in many cases, both will have the same general shape and this shape will be different than the shape of the power output connector 1530a, which need not be circular, to prevent users from attempting to plug an indifferent pad assembly into a power output connector and/or an electrophysiological device into a power return connector. Alternatively, the power output power return connectors could have the same general shape and noticeably different sizes to prevent confusion. Color coding may also be used.

The ESU can be configured to sense current individually to each connection and shut off power if current to either return connection exceeds a predetermined amount, for example 1 ampere. As described elsewhere herein, in some situations for the pad assembly, ablation can occur at the pad assembly, which can correspond to a bipolar mode technique.

In some cases, embodiments of the present invention can incorporate various aspects of treatment systems and methods which are disclosed in previously incorporated U.S. patent application Ser. No. 13/074,867 filed Mar. 29, 2011.

Individual system elements or aspects of a tissue treatment computer system may be implemented in a separated or more integrated manner. In some embodiments treatment systems, which may include computer systems, which may be part of or operatively associated with an electrosurgical unit (ESU) such as the ESU 1540a shown in FIG. 15A, also include software elements, for example located within a working memory of a memory, including an operating system and other code, such as a program designed to implement method embodiments of the present invention. In some cases, software modules implementing the functionality of the methods as described herein, may be stored in a storage subsystem. It is appreciated that systems can be configured to carry out various method aspects described herein. Each of the devices or modules of the present invention can include software modules on a computer readable medium that is processed by a processor, hardware modules, or any combination thereof. Any of a variety of commonly used platforms, such as Windows, MacIntosh, and Unix, along with any of a variety of commonly used programming languages, such as C or C++, may be used to implement embodiments of the present invention. In some cases, tissue treatment systems include FDA validated operating systems or software/hardware modules suitable for use in medical devices. Tissue treatment systems can also include multiple operating systems. For example, a tissue treatment system can include a FDA validated operating system for safety critical operations performed by the treatment system, such as data input, power control, diagnostic procedures, recording, decision making, and the like. A tissue treatment system can also include a non-validated operating system for less critical operations. In some embodiments, a computer system can be in integrated into a tissue treatment system, and in some embodiments, a computer system can be separate from, but in connectivity with, a tissue treatment system. It will be apparent to those skilled in the art that substantial variations may be used in accordance with any specific requirements. For example, customized hardware might also be used and/or particular elements might be implemented in hardware, software (including portable software, such as applets), or both. Further, connection to other computing devices such as network input/output devices may be employed. Relatedly, any of the hardware and software components discussed herein can be integrated with or configured to interface with other medical treatment or information systems used at other locations.

While exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A system for administering ablative radiofrequency electric current therapy to a human patient, comprising:
    an electrosurgical unit assembly having an ablation probe carrying an electrode configured for placement within the patient's left atrial chamber, the electrode configured to transmit an ablative radiofrequency electric current, the electrosurgical unit controlling the temperature at the ablation probe;
    a pad assembly having a thickness sufficiently thin to facilitate insertion between the patient's esophagus and the posterior wall of the patient's left atrium, the pad assembly having a proximal portion, a distal portion, and a tether transition portion, the proximal portion being wider than the distal portion and the tether transition portion, the tether transition portion contacting a tether assembly, the pad assembly having a rounded border, where an entirety of the thickness of the pad assembly has an electrical pad conductivity greater than or equal to an electrical conductivity of the posterior wall of the left atrium to receive the ablative radiofrequency electric current transmitted by the electrode such that thermal damage of the esophagus is inhibited during therapy, where the ablation probe is moveable independent of the pad assembly such that increasing a distance between the ablation probe and the pad assembly spreads the current throughout the patient's left atrial chamber; and
    a return pad configured for placement on the patient's skin, the return pad in operative association with the electrosurgical unit assembly and configured to receive the ablative radiofrequency electric current delivered from the pad assembly.

2. The system according to claim 1, wherein the pad assembly comprises a material having a thermal conductivity value that is within a range from about 0.05 W/m° C. to about 1.0 W/m° C.

3. The system according to claim 1, wherein the pad assembly comprises a pad having an anterior portion and posterior portion on opposing sides of the pad, the posterior portion comprising a posterior portion material with a thermal conductivity value that is within a range from about 0.05 W/m° C. to about 1.0 W/m° C.

4. The system according to claim 1, wherein the pad assembly is positionable between epicardial tissue and pericardial tissue of the patient's heart.

5. The system according to claim 1, wherein the pad assembly comprises an anterior portion and a posterior portion, and the pad assembly is positionable between the patient's atrial wall and esophagus so that the anterior portion faces toward the atrial wall and the posterior portion faces toward the esophagus.

6. A system for administering ablative radiofrequency electric current therapy to a human patient, comprising:
    an electrosurgical unit assembly having an electrode configured for placement at or near a target tissue of the patient, the electrode configured to transmit an ablative radiofrequency electric current, the electrosurgical unit controlling the temperature of the electrode;
    a pad assembly having a thickness suitable for insertion between the patient's target tissue and a protected tissue of the patient, the pad assembly having a proximal portion, a distal portion, and a tether transition portion, the proximal portion being wider than the distal portion and the tether transition portion, the tether transition portion contacting a tether assembly, the protected tissue being adjacent to the target tissue, an entirety of the pad assembly being configured with an electrical pad conductivity greater than or equal to an electrical conductivity of patient's target tissue to receive the ablative radiofrequency electric current transmitted by the electrode during therapy such that thermal damage of the protected tissue is inhibited, the pad assembly having a rounded border; and
    a return pad configured for placement on the patient's skin, the return pad in operative association with the electrosurgical unit assembly and configured to receive the ablative radiofrequency electric current delivered from the pad assembly.

7. A system as in claim 1, wherein the pad assembly comprises a thin pad having a thickness within a range from about 1 mm to 8 mm to facilitate insertion of the thin pad between pulmonary veins or between atrial tissues and the esophagus of the patient.

8. A system as in claim 7 wherein the thin pad varies in thickness such that a thickness at a center is about twice that of a thickness near an edge of the thin pad so as to facilitate placement of the thin pad between pulmonary veins or between atrial tissues and the esophagus of the patient.

9. A system as in claim 7, wherein the thin pad comprises a rounded or curved leading edge so as to facilitate placement of the thin pad between pulmonary veins or between atrial tissues and the esophagus of the patient.

10. A pad assembly for use with a return pad and in an ablative radiofrequency electric current therapy applied to a target tissue of a patient, comprising:
    a pad having a planar thickness sufficiently thin to facilitate insertion between the target tissue and a protected tissue in the patient, the pad having a proximal portion, a distal portion, and a tether transition portion, the proximal portion being wider than the distal portion and the tether transition portion, the tether transition portion contacting a tether assembly, the pad having a rounded border, the pad assembly configured with a first side of the pad assembly having a first electrical conductivity greater than or equal to an electrical conductivity of the target tissue, and where a second side of the pad assembly is thermally insulative and at least semi electrically conductive, such that an entire thickness of the pad assembly is electrically conductive; and where the first side of the pad assembly receives the ablative radiofrequency electric current transmitted by an electrode of an electrosurgical unit assembly during therapy so that thermal damage of the protected tissue is inhibited when the ablative radiofrequency current is transmitted from within the patient to the target tissue while the return pad is on the patient's skin.

11. The pad assembly according to claim 10, wherein the pad comprises a material having a thermal conductivity value that is within a range from about 0.05 W/m° C. to about 1.0 W/m° C.

12. The pad assembly according to claim 10, wherein the pad assembly is positionable between epicardial tissue and pericardial tissue of the patient's heart.

13. The pad assembly according to claim 10, wherein the rounded border surrounds the proximal portion and the distal portion, and wherein the rounded border does not surround the tether transition portion.

14. The pad assembly according to claim 10, wherein the pad comprises an anterior portion and a posterior portion on opposite facing surfaces of the pad such that, when the pad is positioned between the target tissue and the protected tissue in the patient, the anterior portion faces toward the target tissue and the posterior portion faces toward the protected tissue.

15. The pad assembly according to claim 14, wherein the posterior portion comprises a posterior portion material with a thermal conductivity value that is within a range from about 0.05 W/m° C. to about 1.0 W/m° C.

16. The pad assembly according to claim 10, wherein the pad assembly comprises a thin pad having a thickness within a range from about 1 mm to 8 mm to facilitate insertion of the thin pad between the target tissue and the protected tissue in the patient.

17. The pad assembly according to claim 16, wherein the pad varies in thickness such that a thickness at a center is about twice that of a thickness near an edge of the thin pad so as to facilitate placement of the thin pad between the target tissue and the protected tissue in the patient.

18. The pad assembly according to claim 16, wherein the pad comprises a rounded or curved leading edge so as to facilitate placement of the thin pad between the target tissue and the protected tissue in the patient.

19. The pad assembly according to claim 10, wherein the pad is sufficiently hard to inhibit buckling of the pad assembly during insertion between the target tissue and the protected tissue in the patient.

* * * * *